United States Patent
Gottardi et al.

(10) Patent No.: US 11,318,103 B2
(45) Date of Patent: May 3, 2022

(54) TREATING SOFT TISSUE VIA CONTROLLED DRUG RELEASE

(71) Applicants: University of Pittsburgh—Of the Commonwealth System of Higher Education, Pittsburgh, PA (US); Ri.Med Foundation, Palermo (IT)

(72) Inventors: Riccardo Gottardi, Pittsburgh, PA (US); Peter Alexander, Wexford, PA (US); Patrick A. Bianconi, Wexford, PA (US); Steven R. Little, Allison Park, PA (US)

(73) Assignees: University of Pittsburgh—Of the Commonwealth System of Higher Education, Pittsburgh, PA (US); Ri.Med Foundation, Palermo (IT)

( * ) Notice: Subject to any disclaimer, the term of this patent is extended or adjusted under 35 U.S.C. 154(b) by 458 days.

(21) Appl. No.: 16/205,086

(22) Filed: Nov. 29, 2018

(65) Prior Publication Data
US 2019/0142758 A1    May 16, 2019

Related U.S. Application Data

(62) Division of application No. 15/123,994, filed as application No. PCT/US2015/019005 on Mar. 5, 2015, now Pat. No. 10,179,111.

(60) Provisional application No. 61/949,886, filed on Mar. 7, 2014.

(51) Int. Cl.
| | |
|---|---|
| *A61K 9/50* | (2006.01) |
| *A61K 45/06* | (2006.01) |
| *A61K 31/4439* | (2006.01) |
| *A61K 31/519* | (2006.01) |
| *A61K 31/4709* | (2006.01) |
| *A61K 31/496* | (2006.01) |
| *A61K 38/17* | (2006.01) |
| *A61K 35/28* | (2015.01) |
| *A61K 35/32* | (2015.01) |

(52) U.S. Cl.
CPC ........ *A61K 9/5031* (2013.01); *A61K 31/4439* (2013.01); *A61K 31/4709* (2013.01); *A61K 31/496* (2013.01); *A61K 31/519* (2013.01); *A61K 35/28* (2013.01); *A61K 35/32* (2013.01); *A61K 38/17* (2013.01); *A61K 45/06* (2013.01); *Y02A 50/30* (2018.01)

(58) Field of Classification Search
CPC ........ A61K 45/06; A61K 38/17; A61K 35/32; A61K 35/28; A61K 31/519; A61K 31/496; A61K 31/4709; A61K 31/4439; A61K 9/5031
See application file for complete search history.

(56) References Cited

U.S. PATENT DOCUMENTS

| | | |
|---|---|---|
| 8,507,501 B2 | 8/2013 | Yu et al. |
| 2009/0274712 A1* | 11/2009 | Dennis ............... C07K 16/00 424/178.1 |
| 2010/0093760 A1 | 4/2010 | Yu et al. |
| 2011/0053930 A1 | 3/2011 | Yu et al. |
| 2012/0208172 A1 | 8/2012 | Karp et al. |
| 2013/0108594 A1* | 5/2013 | Martin-Rendon ........ A61P 9/10 424/93.21 |
| 2014/0038953 A1 | 2/2014 | Yu et al. |
| 2016/0083690 A1* | 3/2016 | Birch ............... A61L 27/34 424/491 |

FOREIGN PATENT DOCUMENTS

| | | |
|---|---|---|
| WO | WO 2011/019092 | 2/2011 |
| WO | WO 2014/022685 | 2/2014 |

OTHER PUBLICATIONS

Kholodenko et al. (Cells, 2019, 8(10), 1127). (Year: 2019).*
Anderson et al., "Biodegradation and biocompatibility of PLA and PLGA microspheres," *Adv. Drug. Del. Rev.*, 28(1): 5-24, 1997.
Final Office Action issued by U.S. Patent and Trademark Office for U.S. Appl. No. 15/123,994 dated Jan. 10, 2018.
Gupta et al., "Mesenchymal stem cells for cartilage repair in osteoarthritis," *Stem Cell Research & Therapy*, 3(25): 1-9, 2012.
Hong et al., "Applications of small molecule BMP inhibitors in physiology and disease," *Cytokine Growth Factor Rev.* 2009, 20(5-6): 409-411, Nov. 14, 2010.
International Search Report and Written Opinion issued for International Application No. PCT/US2015/019005 dated Jun. 6, 2015.
Non-Final Office Action issued by U.S. Patent and Trademark Office for U.S. Appl. No. 15/123,994 dated Jun. 14, 2017.
YU el al., "BMP type I receptor inhibition reduces heterotropic ossification," *Nature Medicine*, 14(12): 1363-1369, 2008.

* cited by examiner

*Primary Examiner* — Genevieve S Alley
(74) *Attorney, Agent, or Firm* — Klarquist Sparkman, LLP

(57) ABSTRACT

Methods for inhibiting tissue ossification or calcification in a subject, comprising administering a therapeutically effective amount of BMP I inhibitor-loaded microparticles to a subject in need thereof, wherein the administration provides local and sustained release of the BMP I inhibitor thereby inhibiting tissue ossification or calcification.

13 Claims, 12 Drawing Sheets

Microsphere Toxicity
Live/Dead staining
— Shows affect of blank microspheres on MSC growth and proliferation
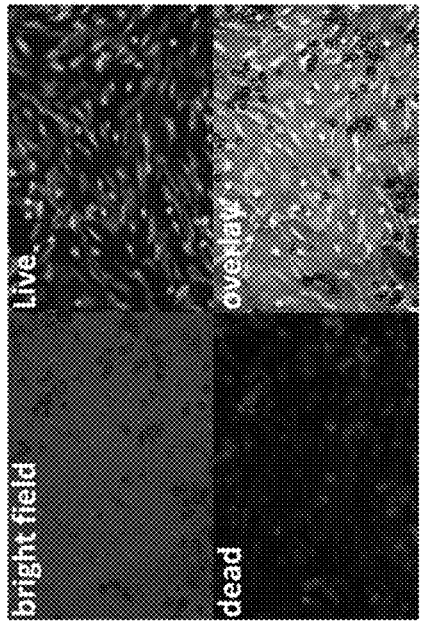
PLGA MPs
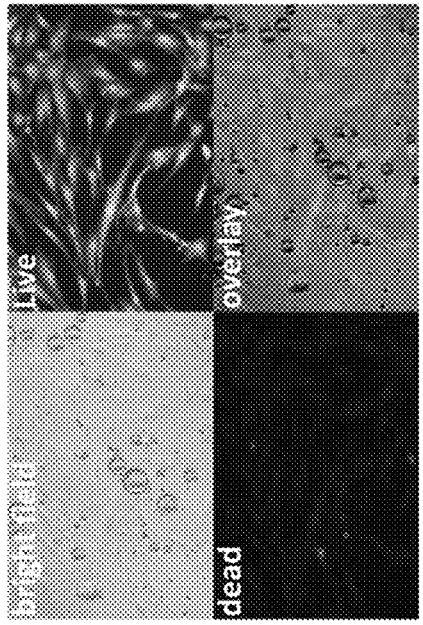
Alginate MPs
FIG. 2

Inducing calcification: Preliminary test

- Test on osteochondral plugs in basal media
- Triiodothyronine (T3) induces calcification
  — calcification prevention with dorsomorphin?

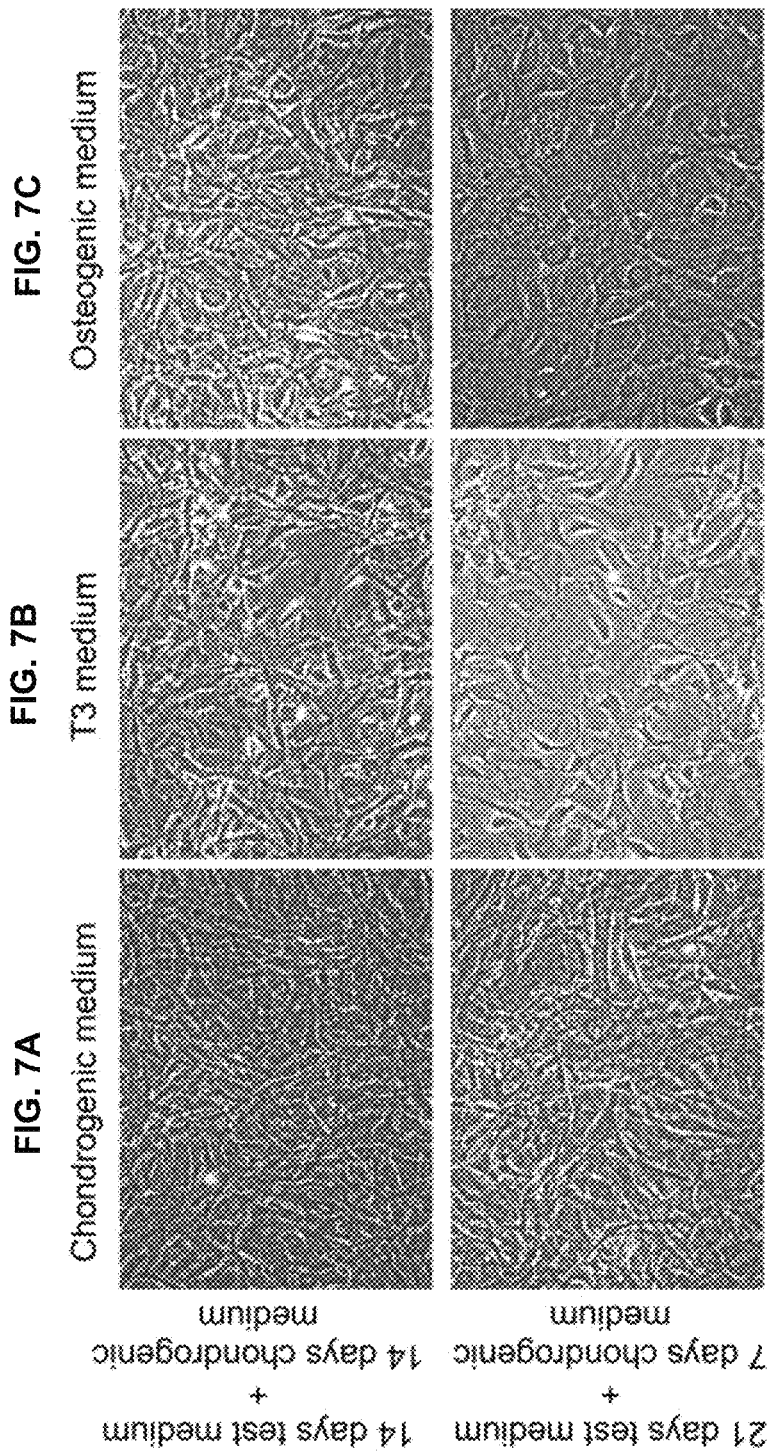

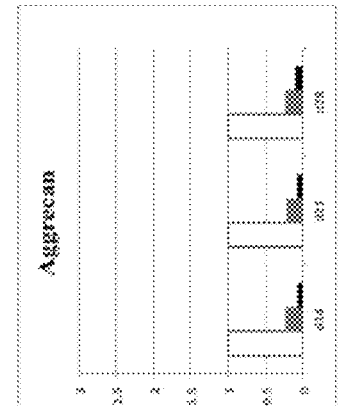
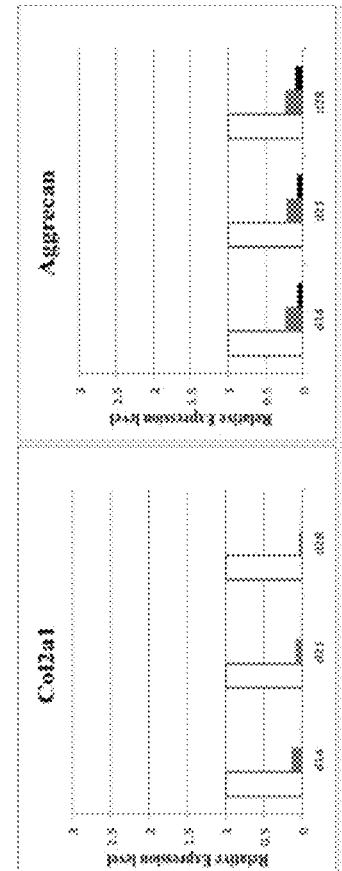
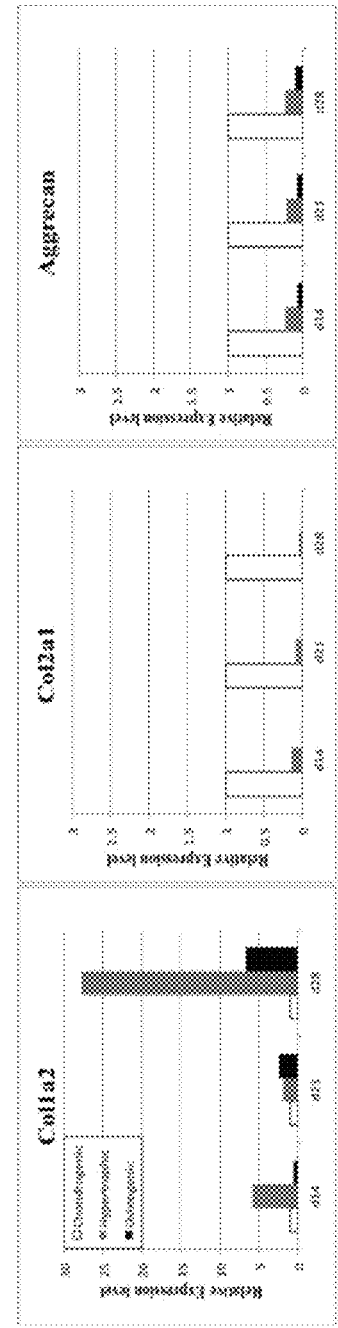
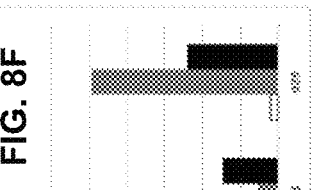
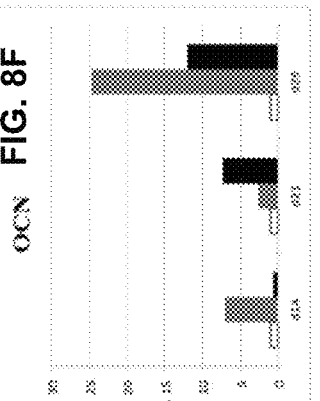
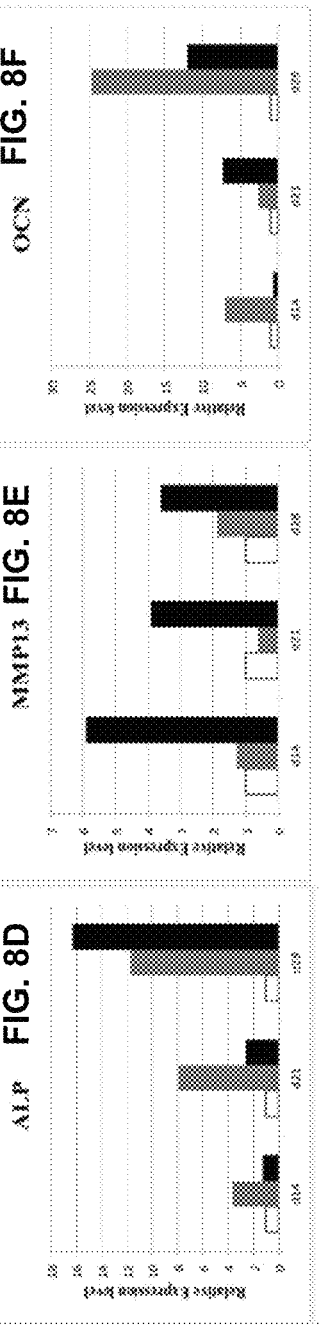
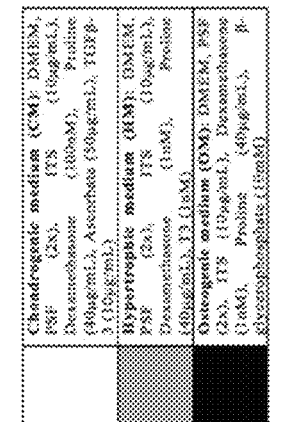
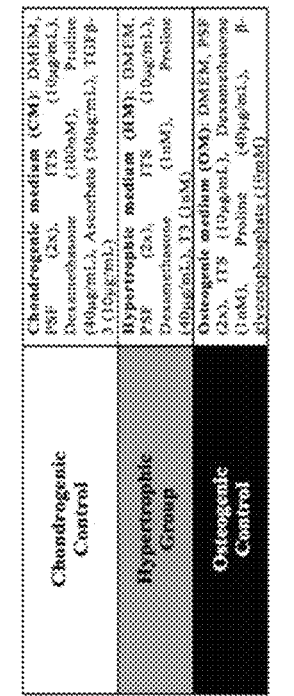

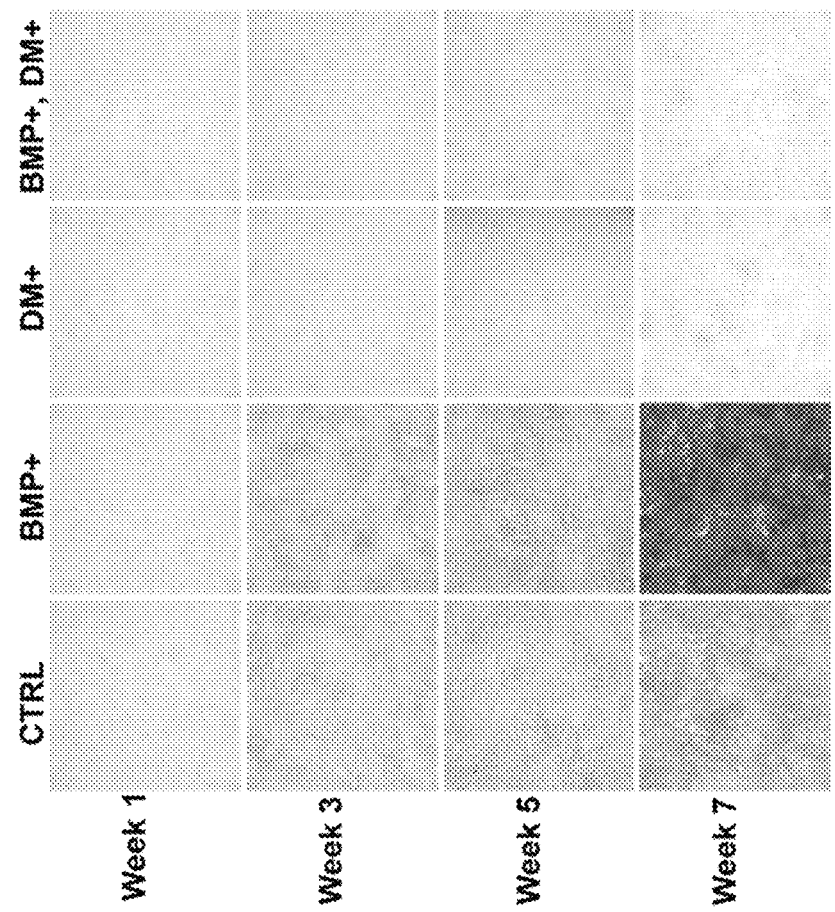

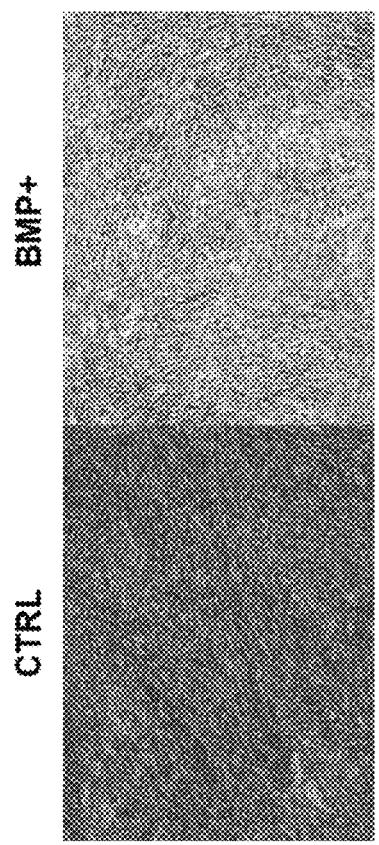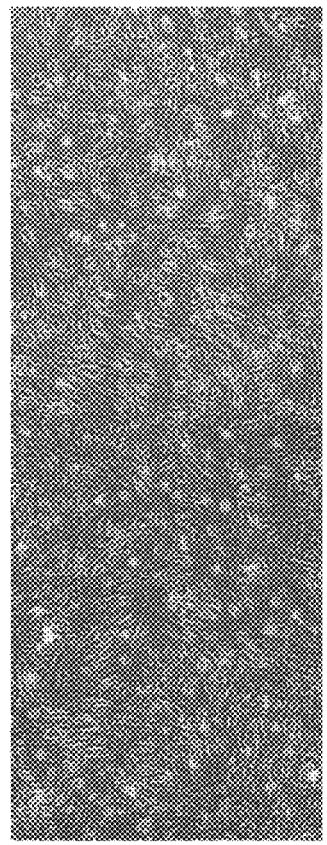

TREATING SOFT TISSUE VIA CONTROLLED DRUG RELEASE

CROSS REFERENCE TO RELATED APPLICATION

This application is a divisional of U.S. application Ser. No. 15/123,994, filed Sep. 6, 2016, which is the U.S. National Stage of International Application No. PCT/US2015/019005, filed Mar. 5, 2015, which was published in English under PCT Article 21(2), which in turn claims the benefit of U.S. Provisional Application No. 61/949,886, filed Mar. 7, 2014, which is incorporated herein by reference in its entirety.

BACKGROUND

The surgical procedures currently used to treat local cartilage damage (focal lesions) are: microfracture (MFX), autologous chondrocyte implantation (ACI), and mesenchymal stem cell (MSC) implantation. Although these procedures produce healthy cartilage, 18% of MFX and 16% of ACI require re-operation because of cartilage calcification, while nearly all MSC treatments exhibit some extent of chondrocyte hypertrophy, which is the initial stage of calcification.

Chondrocyte hypertrophy, the cell terminal differentiation stage, as well as calcification in general, are the result of specific pathways, in particular of SMAD1/5/8 phosphorylation, a canonical BMP pathway. Recently, a small synthetic molecule, dorsomorphin, has been found to interfere with SMAD1/5/8 phosphorylation, thus inhibiting chondrocyte terminal differentiation.

SUMMARY

Disclosed herein are methods for inhibiting tissue ossification or calcification in a subject, comprising administering a therapeutically effective amount of BMP I inhibitor-loaded microparticles to a subject in need thereof, wherein the administration provides local and sustained release of the BMP I inhibitor thereby inhibiting tissue ossification or calcification.

Also disclosed herein are methods comprising administering a therapeutically effective amount of a BMP I inhibitor to a subject in need of cartilage repair, wherein the BMP I inhibitor is locally delivered at the site of the cartilage repair in a sustained release form, and the sustained release form comprises a BMP I inhibitor-loaded microparticles.

Further disclosed herein are methods for inhibiting tissue ossification or calcification in a subject, comprising administering a therapeutically effective amount of inhibitor-loaded microparticles to a subject in need thereof, wherein the administration provides local and sustained release of the inhibitor thereby inhibiting tissue ossification or calcification, and wherein the inhibitor interferes with activation of SMAD 1/5/8.

Additionally disclosed herein are methods comprising administering a therapeutically effective amount of an inhibitor to a subject in need of cartilage repair, wherein the inhibitor is locally delivered at the site of the cartilage repair in a sustained release form, and the sustained release form comprises inhibitor-loaded microparticles and the inhibitor interferes with activation of SMAD 1/5/8.

Also disclosed herein is a therapeutic scaffold comprising (i) BMP I inhibitor-loaded microparticles and (ii) chondrocytes, mesenchymal stem cells, or a combination thereof.

Further disclosed herein is a pharmaceutical composition comprising (i) BMP I inhibitor-loaded microparticles and (ii) at least one pharmaceutically acceptable carrier, adjuvant or excipient.

The foregoing will become more apparent from the following detailed description, which proceeds with reference to the accompanying figures.

BRIEF DESCRIPTION OF THE DRAWINGS

FIG. 2 shows the results of microsphere toxicity testing. Human mesenchymal stem cells have been seeded at a density of $10,000/cm^2$ on a tissue culture treated six well plate with the addition of either alginate or PLGA microparticles. Alginate microparticles served as a control. After two days in culture with growth media (DMEM added with fetal bovine serum and penicillin/streptomycin/fungizone) cells were tested with a LIVE/DEAD® Viability/Cytotoxicity Kit to rapidly discriminates live from dead cells by simultaneously staining with the green-fluorescent calcein-AM and the red-fluorescent ethidium homodimer-1. The first indicates intracellular esterase activity, the latter loss of integrity of the cell plasma membrane. Bright field images are compared with green-fluorescent, red-fluorescent, and overlay images. Microparticles appear as spheres in the bright field image (top left of each panel), live cells are stained green in the green-fluorescent image (top right of each panel), dead cells are stained red in the red-fluorescent image (bottom left panel). Very few red stains are visible for alginate microparticles. More are visible for cells treated with PLGA microparticles, however the red signal does not come from the cells. By comparing the overlay images, it is clear that most of the red fluorescent co-localizes with PLGA microspheres. This suggests that ethidium homodimer-1 partitions into the PLGA polymer, which is not unexpected given the hydrophobic nature of ethidium homodimer-1. In conclusion, PLGA microparticles have minimal if no effect on cell viability.

FIGS. 7A-7F are microphotographs of human chondrocytes. Chondrocytes extracted from human donors have been cultured under a test medium to induce hypertrophy for 14 or 21 days followed by 14 or 7 days of chondrogenic medium, respectively. The test medium was either chondrogenic medium (negative control, no hypertrophy), medium containing triiodothyronine (T3) (hypertrophic), osteogenic medium (hypertrophic).

FIGS. 8A-8G are graphs of gene expression. Human chondrocyte and osteoblasts were cultured for 28 days after seeding in a three-dimensional construct made of photocrosslinkable gelatin at a concentration of 10 million cells/ml. Osteoblasts served as a positive control. Chondrocytes constructs were cultured for 14, 21, or 28 days in chondrogenic or hypertrophic (containing T3) medium, followed by 14, 21, or 0 days, respectively, of culture in chondrogenic medium. Osteoblasts constructs were cultured for 14, 21, or 28 days in osteogenic medium, followed by 14, 21, or 0 days, respectively, of culture in chondrogenic medium. At the end of the 28 days test, all constructs were harvested and RNA extracted to assess expression of chondrogenic genes (Col1a2, and Aggrecan) and of hypertrophic/osteogenic genes (ALP, COLX, MMP13, OCN).

FIG. 10 is microtopographs showing inhibition of muscle-derived multipotent progenitor cells (MPC) osteogenesis in 2D by 2.5 nM of dorsomorphin (DM) as shown by alizarin red staining (magnification 10×). Osteogenesis was induced by addition of BMP to the medium.

FIGS. 11A and 11B are microphotographs of bone marrow-derived mesenchymal stem cells (BMD-MSCs) showing inhibition of BMD-MSC osteogenesis in 2D culture by dorsomorphin (DM). Phase contrast images of alizarin red stained cultures treated with BMP, DM, and BMP+DM as compared to control and DM cultures.

DETAILED DESCRIPTION

Terminology

Figure 1:
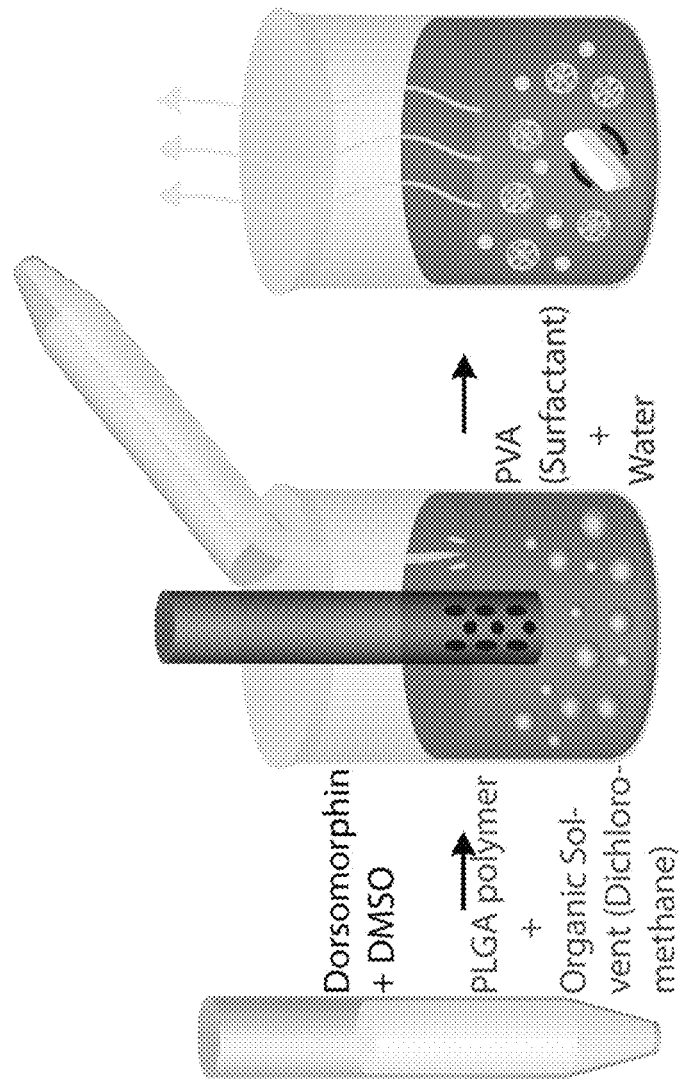
FIG. 1 is a representation of microsphere fabrication.
Figure 3:
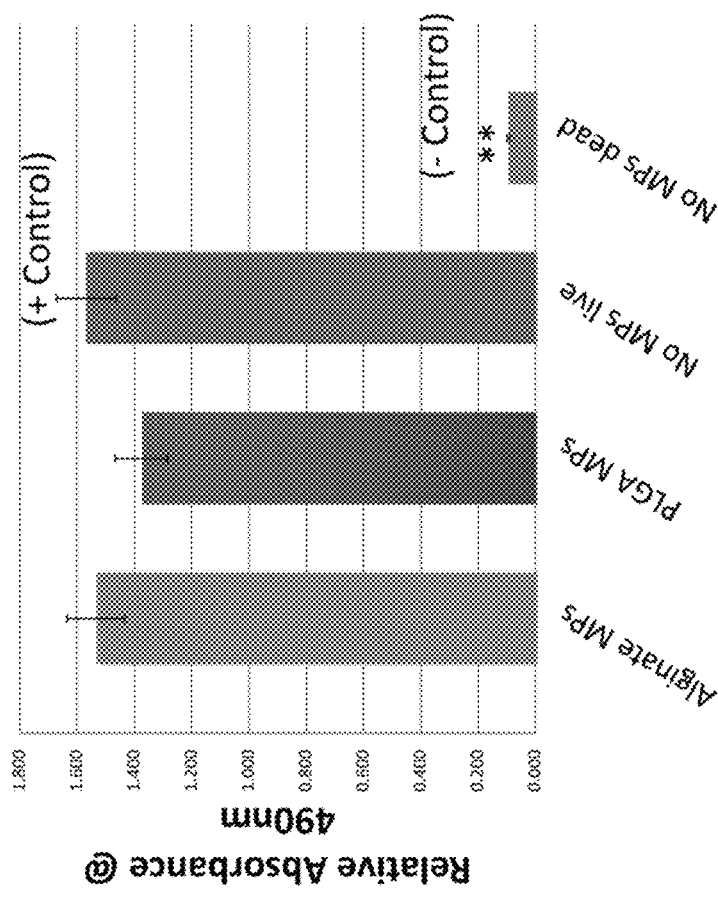
FIG. 3 is a graph depicting the results of metabolic activity of microspheres tested with an MTS assay. This test included the same groups as in FIG. 2 plus a positive control (cells seeded without microparticles) and a negative control (cells treated with methanol for 45 minutes to ensure 100% cell death). All groups were tested with CellTiter 96® AQueous One Solution Cell Proliferation Assay (MTS) to determine colorimetrically any change in the number of viable, metabolically active cells. Test was performed as per the assay protocol. No significant change was observed in cells cultured with either alginate or PLGA microparticles, with only a minor decrease in metabolic signal for cells cultured with PLGA. This is a common feature usually ascribed to the slightly acidic degradation products of the PLGA microparticles. In conclusion, PLGA microparticles have minimal effect on cells metabolic activity.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats.

The term "co-administration" or "co-administering" refers to administration of an agent disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the microparticles disclosed herein.

"Inhibiting" refers to inhibiting the full development of a disease or condition. "Inhibiting" also refers to any quantitative or qualitative reduction in biological activity or binding, relative to a control.

"Microparticle", as used herein, unless otherwise specified, generally refers to a particle of a relatively small size, but not necessarily in the micron size range. In certain embodiments, microparticles specifically refers to particles having a diameter from about 0.01 to about 500 microns, preferably from about 1 to about 200 microns, more preferably from about 5 to about 20 microns. As used herein, the microparticle encompasses microspheres, microcapsules and microparticles, unless specified otherwise. A microparticle may be of composite construction and is not necessarily a pure substance; it may be spherical or any other shape.

Preventing" a disease or condition refers to prophylactic administering a composition to a subject who does not exhibit signs of a disease or condition for the purpose of decreasing the risk of developing a pathology or condition, or diminishing the severity of a pathology or condition.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" also refers to inhibiting the full development of a disease.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—, preferably alkylC(O)NH—.

The term "acyloxy" is art-recognized and refers to a group represented by the general formula hydrocarbylC(O)O—, preferably alkylC(O)O—.

The term "aliphatic", as used herein, includes straight, chained, branched or cyclic hydrocarbons which are completely saturated or contain one or more units of unsaturation. Aliphatic groups may be substituted or unsubstituted.

The term "alkoxy" refers to an oxygen having an alkyl group attached thereto. Representative alkoxy groups include methoxy, ethoxy, propoxy, tert-butoxy and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term "amide", as used herein, refers to a group

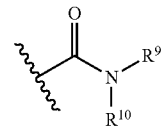

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

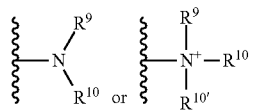

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "carbamate" is art-recognized and refers to a group

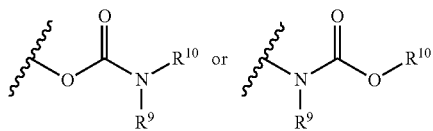

wherein $R^9$ and $R^{10}$ independently represent hydrogen or a hydrocarbyl group, such as an alkyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—R$^9$, wherein R$^9$ represents a hydrocarbyl group, such as an alkyl group.

The term "carboxy", as used herein, refers to a group represented by the formula —CO$_2$H.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "ester", as used herein, refers to a group —C(O)OR$^9$ wherein R$^9$ represents a hydrocarbyl group, such as an alkyl group or an aralkyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen", as used herein, means halogen and includes chloro, fluoro, bromo, and iodo.

The term "heteroalkyl", as used herein, refers to a saturated or unsaturated chain of carbon atoms including at least one heteroatom (e.g., O, S, or NR$^{50}$, such as where R$^{50}$ is H or lower alkyl), wherein no two hetero atoms are adjacent.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitation aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Preferred polycycles have 2-3 rings. Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulthydryl, an alkylthio, a sulfate, a sulfonate, a sulfamoyl, a sulfonamido, a sulfonyl, a heterocyclyl, an aralkyl, or an aromatic or hetero aromatic moiety.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt or ester thereof.

The term "sulfonamide" is art-recognized and refers to the group represented by the general formulae

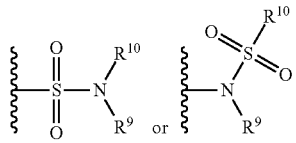

wherein R$^9$ and R$^{10}$ independently represents hydrogen or hydrocarbyl, such as alkyl.

The term "sulfoxide" is art-recognized and refers to the group —S(O)—R$^9$, wherein R$^9$ represents a hydrocarbyl, such as alkyl, aryl, or heteroaryl.

The term "sulfonate" is art-recognized and refers to the group —SO$_3$H, or a pharmaceutically acceptable salt or ester thereof.

The term "sulfone" is art-recognized and refers to the group —S(O)$_2$—R$^9$, wherein R$^9$ represents a hydrocarbyl, such as alkyl, aryl, or heteroaryl.

The term "thioester", as used herein, refers to a group —C(O)SR$^9$ or —SC(O)R$^9$ wherein R$^9$ represents a hydrocarbyl, such as alkyl.

The term "thioether", as used herein, is equivalent to an ether, wherein the oxygen is replaced with a sulfur.

The term "urea" is art-recognized and may be represented by the general formula

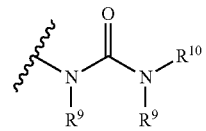

wherein R$^9$ and R$^{10}$ independently represent hydrogen or a hydrocarbyl, such as alkyl.

Overview

There is currently no method to prevent ossification of soft tissue. In particular, in clinical procedures of small defects cartilage repair, cartilage calcification can be a secondary, undesirable effect. The systems and methods disclosed herein would allow avoidance of cartilage calcification. It could also be applied to a number of other instances of calcification of other soft tissues (blood vessels, skin, kidney, tendons, etc.). It is designed to be a local therapy to minimize the issues otherwise related to systemic exposure.

Agents that inhibit bone morphogenetic protein (BMP) type I receptor activity, particularly those that interfere with activation of BMP signaling effectors SMAD 1/5/8, could be used in the local sustained release delivery systems disclosed herein. Illustrative agents include dorsomorphin, LDN-193189 (Yu et al, Nature Medicine, 14:12, 1363-1369, 2008), SB505124, noggin, cordin, and gremlin.

Illustrative inhibitors also include compounds represented by formula I:

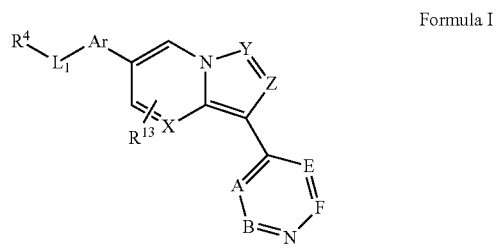

Formula I wherein X is selected from CR$^{15}$ and N; Y is selected from CR$^{15}$ and N; Z is selected from CR$^3$ and N; Ar is selected from substituted or unsubstituted aryl and heteroaryl, e.g., a six-membered ring, such as phenyl; L$_1$ is absent or selected from substituted or unsubstituted alkyl and heteroalkyl; A and B, independently for each occurrence, are selected from CR$^{16}$ and N, preferably CR$^{16}$, e.g., CH; E and F, independently for each occurrence, are selected from CR$^5$ and N, preferably CR$^5$; preferably chosen such that no more than two of A, B, E, and F are N; R$^3$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl; R$^4$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl; $R^5$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^5$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring; $R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably substituted or unsubstituted alkyl, heteroalkyl, halogen, hydroxyl, alkoxyl, alkylthio, acyloxy, acylamino, carbamate, or cyano; $R^{15}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano; $R^{16}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano, or a pharmaceutically acceptable salt, ester, or prodrug thereof.

In certain embodiments, either Y is N or Ar comprises a nitrogen atom in the ring.

In certain embodiments, E and F are each $CR^5$, and both instances of $R^5$ together with the intervening atoms form a 5-, 6-, or 7-membered ring optionally substituted by substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano). In certain embodiments, E and F together form a substituted or unsubstituted 6-membered cycloalkyl, heterocyclyl, aryl or heteroaryl ring (e.g., a pyridine, piperidine, pyran, or piperazine ring, etc.). In certain such embodiments, the ring comprises one to four amine groups, while in other embodiments, the ring is a substituted or unsubstituted benzo ring (e.g.,

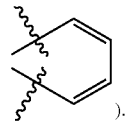

).

In certain such embodiments, the ring is substituted, e.g., by optionally substituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, Ar represents substituted or unsubstituted heteroaryl e.g., pyrrole, furan, thiophene, imidazole, oxazole, thiazole, pyrazole, pyridine, pyrazine, pyridazine, quinoline, and pyrimidine, In certain embodiments, Ar represents substituted or unsubstituted aryl, such as phenyl. In certain embodiments, Ar is a 6-membered ring, such as a phenyl ring, e.g., in which $L_1$ is disposed on the para-position of Ar relative to the bicyclic core.

In certain embodiments as discussed above, substituents on Ar are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_1$ represents a linker $M_k$, wherein k is an integer from 1-8, preferably from 2-4, and each M represents a unit selected from $C(R^{18})_2$, $NR^{19}$, S, $SO_2$, or O, preferably selected so that no two heteroatoms occur in adjacent positions, more preferably with at least two carbon atoms between any nitrogen atom and another heteroatom; wherein $R^{18}$, independently for each occurrence, is selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{19}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl.

In certain embodiments, $L_1$ is absent. In certain embodiments, $L_1$ is selected from substituted or unsubstituted alkyl (e.g., $C_1$-$C_8$ chains, preferably $C_2$-$C_4$ chains) and heteroalkyl. In certain such embodiments, $L_1$ has a structure

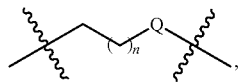

wherein n is an integer from 0 to 4, and Q is selected from $CR^{10}R^{11}NR^{12}$, S, S(O), and $SO_2$; $R^{10}$ and $R^{11}$, independently for each occurrence, are selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{12}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl. In certain embodiments, $L_1$ has a structure

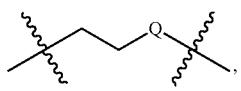

wherein Q is $CH_2$, NH, S, $SO_2$, or O, preferably O.

In certain embodiments, $R^4$ is

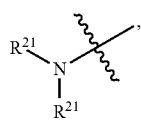

wherein $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain embodiments, $R^4$ is heterocyclyl, e.g., comprising one or two heteroatoms, such as N, S or O (e.g., piperidine, piperazine, pyrrolidine, morpholine, lactone, or lactam). In certain such embodiments, $R^4$ is heterocyclyl comprising one nitrogen atom, e.g., piperidine or pyrrolidine, such as

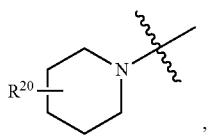

wherein $R^{20}$ is absent or represents from 1-4 substituents on the ring to which it is attached, e.g., selected from substituted or unsubstituted alkyl, heteroaryl, aralkyl, cycloalkyl, heterocyclyl, aryl, heteroaryl, heteroaralkyl, cycloalkylalkyl, heterocyclylalkyl, acyl, hydroxyl, alkoxyl, alkylthio, acyloxy, sulfonyl, sulfoxido, sulfamoyl, and sulfonamido, preferably H or lower alkyl. In certain embodiments, $R^4$ is heterocyclyl comprising two nitrogen atoms, e.g., piperazine. In certain embodiments, $R^4$ is heterocyclyl comprising a nitrogen and an oxygen atom, e.g., morpholine.

In certain embodiments, $R^4$ is a heterocyclyl or heteroaryl that includes an amine within the atoms of the ring, e.g., pyridyl, imidazolyl, pyrrolyl, piperidyl, pyrrolidyl, piperazyl, oxazolyl, isoxazolyl, thiazolyl, etc., and/or bears an amino substituent. In certain embodiments, $R^4$ is

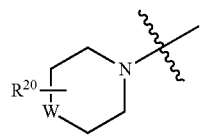

wherein $R^{20}$ is as defined above; W represents a bond or is selected from $C(R^{21})_2$, O, or $NR^{21}$; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain preferred embodiments, $L_1$ is absent and $ArR^4$ has a structure

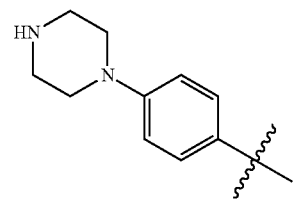

In certain embodiments as discussed above, substituents on $R^4$ are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_1$ is absent and $R^4$ is directly attached to Ar. In embodiments wherein $R^4$ is a six-membered ring directly attached to Ar and bears an amino substituent at the 4-position of the ring relative to N.

In certain embodiments, $L_1$-$R^4$ comprises a basic nitrogen-containing group, e.g., either $L_1$ comprises nitrogen-containing heteroalkyl or an amine-substituted alkyl, or $R^4$ comprises a substituted or unsubstituted nitrogen-containing heterocyclyl or heteroaryl and/or is substituted with an amine substituent. In certain such embodiments, the $pK_a$ of the conjugate acid of the basic nitrogen-containing group is 6 or higher, or even 8 or higher.

In certain embodiments, $L_1$ has a structure

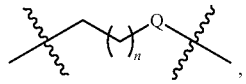

wherein n is an integer from 0 to 4, and $R^4$ is heterocyclyl. In certain such embodiments, E and F together form a ring, e.g., a benzo ring, while in other embodiments, E and F do not form a ring.

In certain embodiments, $L_1$ is absent and $R^4$ is heterocyclyl, especially a nitrogen-containing heterocyclyl. In certain such embodiments, E and F together form a ring, e.g., a benzo ring, while in other embodiments, E and F do not form a ring. In certain embodiments, L₁ is absent and R⁴ is piperidine, piperazine, pyrrolidine, or morpholine.

In certain of the embodiments disclosed above, if L₁ is alkyl or heteroalkyl and R⁴ is heterocyclyl, especially a nitrogen-containing heterocyclyl, then E and F together form a ring, e.g., a benzo ring. In certain of the embodiments disclosed above, if L₁ has a structure

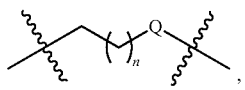

wherein n is an integer from 0 to 4 (especially from 1-2) and Q is S or O, then E and F together form a ring, e.g., a benzo ring.

In certain embodiments, either E and F are both CR⁵ and both occurrences of R⁵ taken together with E and F form a ring, e.g., a benzo ring, or L₁ is absent. In certain such embodiments, R⁴ is selected from substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, and sulfonamido. In certain embodiments, either E and F are both CR⁵ and both occurrences of R⁵ taken together with E and F form a ring, e.g., a benzo ring, or R⁴ is selected from substituted or unsubstituted cycloalkyl, aryl, heteroaryl, acyl, carboxyl, ester, acyloxy, amino, acylamino, carbamate, amido, amidino, sulfonyl, sulfoxido, sulfamoyl, and sulfonamido.

In certain of the embodiments disclosed above, if L₁ is absent, R⁴ is cycloalkyl or heterocyclyl (e.g., a nitrogen-containing heterocycle, such as piperidine, piperazine, pyrrolidine, morpholine, etc.).

In certain of the embodiments disclosed above, if L₁ is heteroalkyl and R⁴ is heterocyclyl (especially a nitrogen-containing heterocycle), then Y is CR¹⁵, wherein R¹⁵ is as defined above. In certain of the embodiments disclosed above, if L₁ is heteroalkyl and R⁴ is piperidine, then Y is CR¹⁵, wherein R¹⁵ is as defined above. In certain embodiments wherein Y is CR¹⁵, R¹⁵ is selected from H, lower alkyl, heteroalkyl, and ester (e.g., lower alkyl ester, such as methyl ester).

In certain of the embodiments disclosed above, if L₁ is heteroalkyl and R⁴ is heterocyclyl (especially nitrogen-containing heterocyclyl), then X is CR¹⁵, wherein R¹⁵ is as defined above. In certain of the embodiments disclosed above, if L₁ is heteroalkyl and R⁴ is piperidine, then X is CR¹⁵, wherein R¹⁵ is as defined above. In certain embodiments wherein X is R¹⁵, R¹⁵ is selected from H, lower alkyl, and hetero alkyl.

In certain of the embodiments disclosed above, if L₁ is heteroalkyl and R⁴ is heterocyclyl (especially nitrogen-containing heterocyclyl), then Z is CR³, wherein R³ is as defined above. In certain of the embodiments disclosed above, if L₁ is heteroalkyl and R⁴ is piperidine, then Z is CR³, wherein R³ is as defined above. In certain embodiments Z is CR³, R³ is selected from H, lower alkyl, and hetero alkyl.

In certain of the embodiments disclosed above, if L₁ is heteroalkyl and R⁴ is heterocyclyl (especially a nitrogen-containing heterocycle, such as piperidine), R¹³ represents 2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido.

In certain of the embodiments disclosed above, if L₁ is heteroalkyl and R⁴ is heterocyclyl (especially a nitrogen-containing heterocycle, such as piperidine), Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine). In certain such embodiments, Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, if L₁ is heteroalkyl and R⁴ is heterocyclyl (e.g., piperidine, piperazine, pyrrolidine, morpholine, lactones, lactams, and the like), R⁴ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, compounds have one or more of the following features:

either Y is N or Ar comprises a nitrogen atom in the ring;

L₁ is absent;

E and F together form a ring;

R⁴ is cycloalkyl, aryl, or heteroaryl;

X is CR¹⁵;

Y is CR¹⁵;

Z is CR³;

R¹³ represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido;

Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine);

Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido; and R⁴ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In one aspect, the compounds that inhibit BMP-induced phosphorylation of SMAD1/5/8 including compounds represented by general formula II

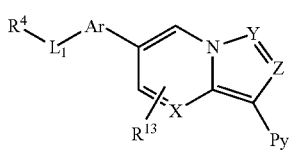

wherein X is selected from $CR_{15}$ and N; Y is selected from $CR_{15}$ and N; Z is selected from $CR_3$ and N; Ar is selected from substituted or unsubstituted aryl and heteroaryl, e.g., a six-membered ring, such as phenyl; $L_1$ is absent or selected from substituted or unsubstituted alkyl and heteroalkyl; Py is substituted or unsubstituted 4-pyridinyl or 4-quinolinyl, e.g., optionally substituted with substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, amino, acylamino, carbamate, amido, amidino, cyano, sulfonyl, sulfoxido, sulfamoyl, or sulfonamido; and $R^3$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl; $R^4$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl; $R^5$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^3$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring; $R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably substituted or unsubstituted alkyl, heteroalkyl, halogen, hydroxyl, alkoxyl, alkylthio, acyloxy, acylamino, carbamate, or cyano; $R^{15}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano; $R^{16}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano, or a pharmaceutically acceptable salt, ester, or prodrug thereof.

In certain embodiments, either Y is N or Ar comprises a nitrogen atom in the ring.

In certain embodiments, Py is substituted by substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, Ar represents substituted or unsubstituted heteroaryl e.g., pyrrole, furan, thiophene, imidazole, oxazole, thiazole, pyrazole, pyridine, pyrazine, pyridazine, quinoline, and pyrimidine. In certain embodiments, Ar represents substituted or unsubstituted aryl, such as phenyl. In certain embodiments, Ar is a 6-membered ring, such as a phenyl ring, e.g., in which $L_1$ is disposed on the para-position of Ar relative to the bicyclic core.

In certain embodiments as discussed above, substituents on Ar are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_1$ represents a linker $M_k$, wherein k is an integer from 1-8, preferably from 2-4, and each M represents a unit selected from $C(R^{18})_2$, $NR^{19}$, S, $SO_2$, or O, preferably selected so that no two heteroatoms occur in adjacent positions, more preferably with at least two carbon atoms between any nitrogen atom and another heteroatom; wherein $R^{18}$, independently for each occurrence, is selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{19}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl.

In certain embodiments, $L_1$ is absent. In certain embodiments, $L_1$ is selected from substituted or unsubstituted alkyl (e.g., $C_1$-$C_8$ chains, preferably $C_2$-$C_4$ chains) and heteroalkyl. In certain such embodiments, $L_1$ has a structure

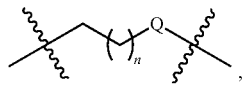

wherein n is an integer from 0 to 4, and Q is selected from $CR^{10}R^{11}$, $NR^{12}$, S, S(O), and $SO_2$; $R^{10}$ and $R^{11}$, independently for each occurrence, are selected from H and substituted or unsubstituted alkyl, heteroalkyl, cycloalkyl, heterocyclyl, cycloalkylalkyl, heterocyclylalkyl, hydroxyl, alkoxyl, alkylthio, acyloxy, amino, acylamino, carbamate, amido, amidino, cyano, sulfonyl, sulfoxido, sulfamoyl, or sulfonamido, preferably H or lower alkyl; and $R^{12}$ is selected from H and substituted or unsubstituted alkyl, cycloalkyl, heterocyclyl, heterocyclylalkyl, oxide, amino, acylamino, carbamate, amido, amidino, sulfonyl, sulfamoyl, or sulfonamido, preferably H or lower alkyl. In certain embodiments, $L_1$ has a structure

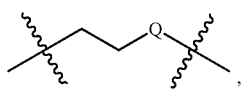

wherein Q is $CH_2$, NH, S, $SO_2$, or O, preferably O. In certain embodiments, $R^4$ is

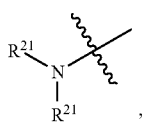

wherein $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain embodiments, $R^4$ is heterocyclyl, e.g., comprising one or two heteroatoms, such as N, S or O (e.g., piperidine, piperazine, pyrrolidine, morpholine, lactone, or lactam). In certain such embodiments, $R^4$ is heterocyclyl comprising one nitrogen atom, e.g., piperidine or pyrrolidine, such as

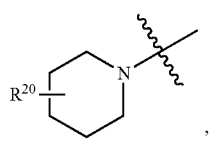

wherein $R^{20}$ is absent or represents from 1-4 substituents on the ring to which it is attached, e.g., selected from substituted or unsubstituted alkyl, heteroaryl, aralkyl, cycloalkyl, heterocyclyl, aryl, heteroaryl, heteroaralkyl, cycloalkylalkyl, heterocyclylalkyl, acyl, hydroxyl, alkoxyl, alkylthio, acyloxy, sulfonyl, sulfoxido, sulfamoyl, and sulfonamido, preferably H or lower alkyl. In certain embodiments, $R^4$ is heterocyclyl comprising two nitrogen atoms, e.g., piperazine. In certain embodiments, $R^4$ is heterocyclyl comprising a nitrogen and an oxygen atom, e.g., morpholine.

In certain embodiments, $R^4$ is a heterocyclyl or heteroaryl that includes an amine within the atoms of the ring, e.g., pyridyl, imidazolyl, pyrrolyl, piperidyl, pyrrolidyl, piperazyl, oxazolyl, isoxazolyl, thiazolyl, etc., and/or bears an amino substituent. In certain embodiments, $R^4$ is

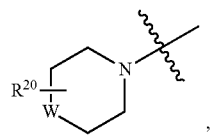

wherein $R^{20}$ is as defined above; W represents a bond or is selected from $C(R^{21})_2$, O, or $NR^{21}$; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido, preferably H or lower alkyl.

In certain embodiments as discussed above, substituents on $R^4$ are selected from substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano).

In certain embodiments, $L_1$ is absent and $R^4$ is directly attached to Ar. In embodiments wherein $R^4$ is a six-membered ring directly attached to Ar and bears an amino substituent at the 4-position of the ring relative to N, the N and amine substituents may be disposed trans on the ring.

In certain embodiments, $L_1$-$R^4$ comprises a basic nitrogen-containing group, e.g., either $L_1$ comprises nitrogen-containing heteroalkyl or an amine-substituted alkyl, or $R^4$ comprises a substituted or unsubstituted nitrogen-containing heterocyclyl or heteroaryl and/or is substituted with an amine substituent. In certain such embodiments, the $pK_a$ of the conjugate acid of the basic nitrogen-containing group is 6 or higher, or even 8 or higher.

In certain embodiments, $L_1$ has a structure

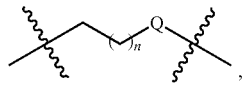

wherein n is an integer from 0 to 4, and $R^4$ is heterocyclyl. In certain such embodiments, Py is 4-quinolinyl, while in other embodiments, Py is 4-pyridinyl.

In certain embodiments, $L_1$ is absent and $R^4$ is heterocyclyl, especially a nitrogen-containing heterocyclyl. In certain such embodiments, Py is 4-quinolinyl, while in other embodiments, Py is 4-pyridinyl. In certain embodiments, $L_1$ is absent and $R^4$ is piperidine, piperazine, pyrrolidine, or morpholine.

In certain of the embodiments disclosed above, if $L_1$ is alkyl or heteroalkyl and $R^4$ is heterocyclyl, especially a nitrogen-containing heterocyclyl, then Py is 4-quinolinyl. In certain of the embodiments disclosed above, if $L_1$ has a structure

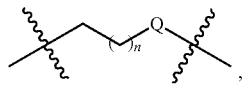

wherein n is an integer from 0 to 4 (especially from 1-2) and Q is S or O, then Py is 4-quinolinyl.

In certain embodiments, either Py is 4-quinolinyl, or $L_1$ is absent. In certain such embodiments, $R^4$ is selected from substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, and sulfonamido. In certain embodiments, either Py is 4-quinolinyl, or $R^4$ is selected from substituted or unsubstituted cycloalkyl, aryl, heteroaryl, acyl, carboxyl, ester, acyloxy, amino, acylamino, carbamate, amido, amidino, sulfonyl, sulfoxido, sulfamoyl, and sulfonamido.

In certain of the embodiments disclosed above, if $L_1$ is absent, $R^4$ is cycloalkyl or heterocyclyl (e.g., a nitrogen-containing heterocycle, such as piperidine, piperazine, pyrrolidine, morpholine, etc.).

In certain of the embodiments disclosed above, if $L_1$ is heteroalkyl and $R^4$ is heterocyclyl (especially a nitrogen-containing heterocycle), then Y is $CR^{15}$, wherein $R^{15}$ is as defined above. In certain of the embodiments disclosed above, if $L_1$ is heteroalkyl and $R^4$ is piperidine, then Y is $CR^{15}$, wherein $R^{15}$ is as defined above. In certain embodiments wherein Y is $CR^{15}$, $R^{15}$, is selected from H, lower alkyl, heteroalkyl, and ester (e.g., lower alkyl ester, such as methyl ester).

In certain of the embodiments disclosed above, if $L_1$ is heteroalkyl and $R^4$ is heterocyclyl (especially nitrogen-containing heterocyclyl), then X is $CR^{15}$, wherein $R^{15}$ is as defined above. In certain of the embodiments disclosed above, if $L_1$ is heteroalkyl and $R^4$ is piperidine, then X is $CR^{15}$, wherein $R^{15}$ is as defined above. In certain embodiments wherein X is $R^{15}$, $R^{15}$ is selected from H, lower alkyl, and hetero alkyl.

In certain of the embodiments disclosed above, if $L_1$ is heteroalkyl and $R^4$ is heterocyclyl (especially nitrogen-containing heterocyclyl), Z is $CR^3$, wherein $R^3$ is as defined above. In certain of the embodiments disclosed above, if $L_1$ is heteroalkyl and $R^4$ is piperidine, then Z is $CR^3$, wherein $R^3$ is as defined above. In certain embodiments wherein Z is $CR^3$, $R^3$ is selected from H, lower alkyl, and heteroalkyl.

In certain of the embodiments disclosed above, if $L_1$ is heteroalkyl and $R^4$ is heterocyclyl (especially a nitrogen-containing heterocycle, such as piperidine), $R^{13}$ represents 2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido.

In certain of the embodiments disclosed above, if $L_1$ is heteroalkyl and $R^4$ is heterocyclyl (especially a nitrogen-containing heterocycle, such as piperidine), Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine). In certain such embodiments, Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, if $L_1$ is heteroalkyl and $R^4$ is heterocyclyl (e.g., piperidine, piperazine, pyrrolidine, morpholine, lactones, lactams, and the like), $R^4$ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In certain of the embodiments disclosed above, compounds have one or more of the following features:
either Y is N or Ar comprises a nitrogen atom in the ring;
$L_1$ is absent;
Py is 4-quinolinyl;
$R_4$ is cycloalkyl, aryl, or heteroaryl;
X is $CR^{15}$;
Y is $CR^{15}$;
Z is $CR^3$;
$R^{13}$ represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido;
Ar represents substituted or unsubstituted heteroaryl (e.g., pyrrole, furan, thiophene, imidazole, oxazole, thiazole, pyrazole, pyridine, pyrazine, pyridazine, quinoline, and pyrimidine);
Ar is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido; and
$R^4$ is substituted with one or more substituents selected from alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamide.

Illustrative compounds of Formula I and Formula II include:

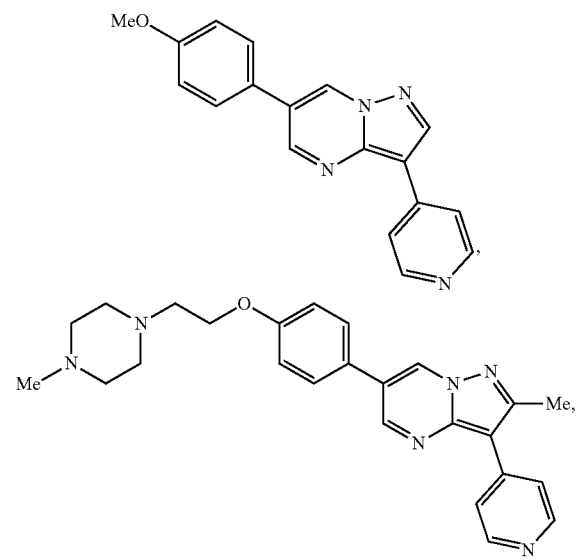

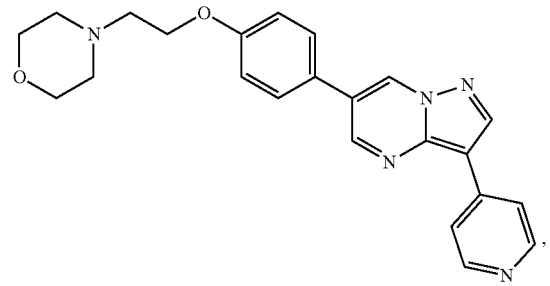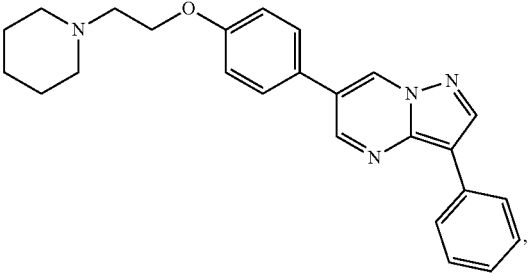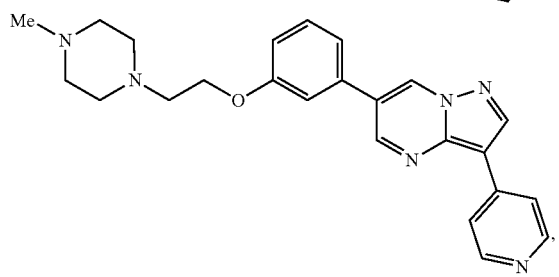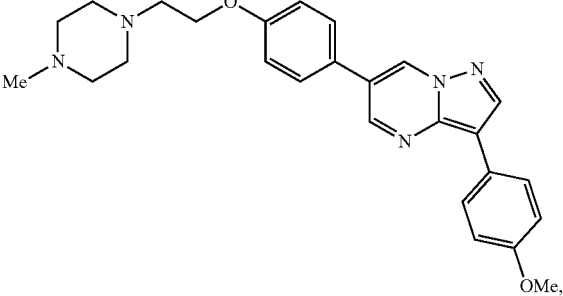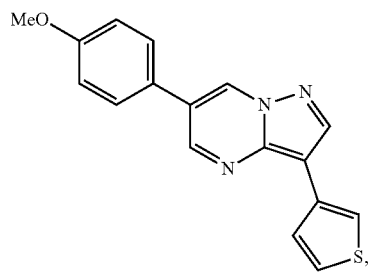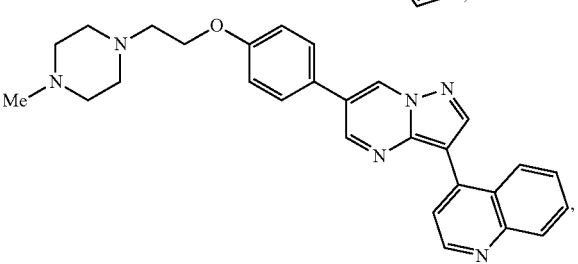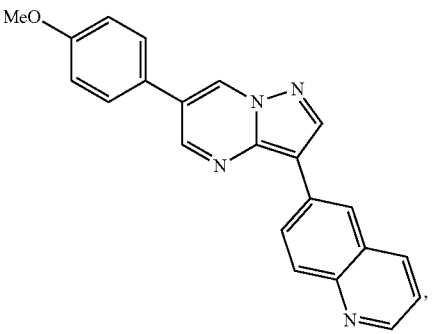

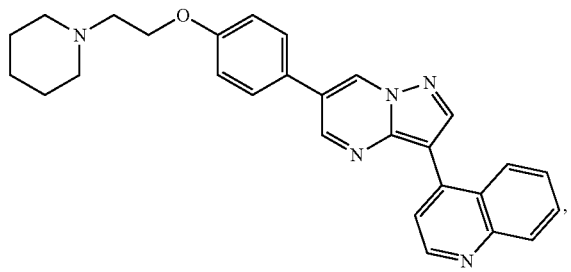
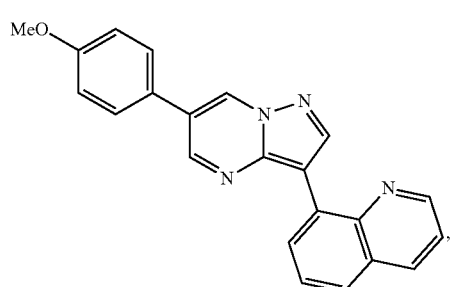
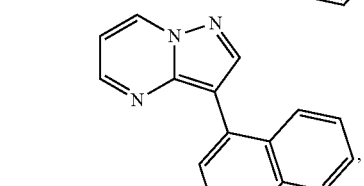
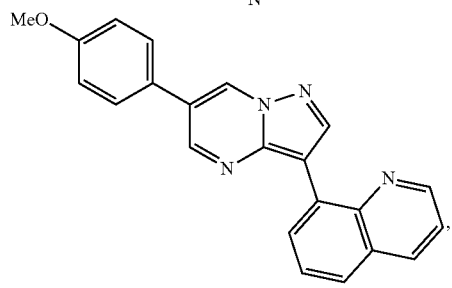
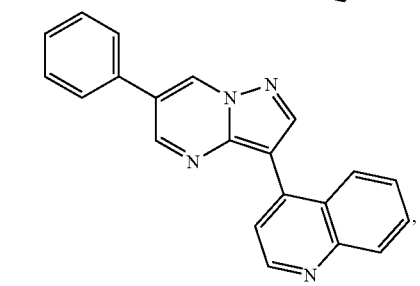
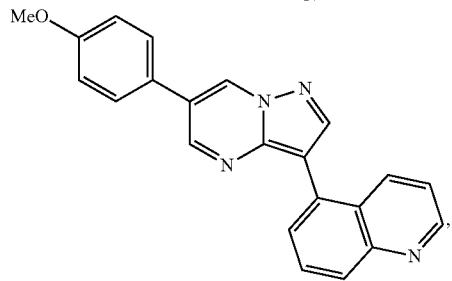
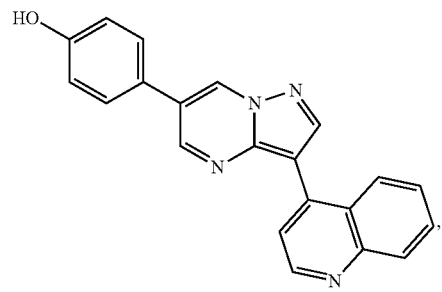
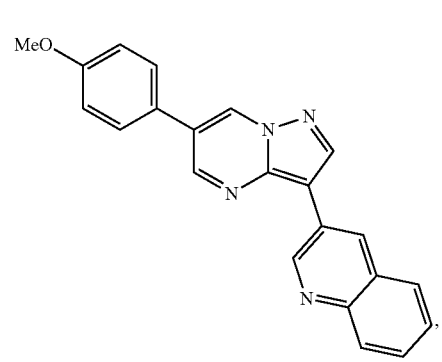
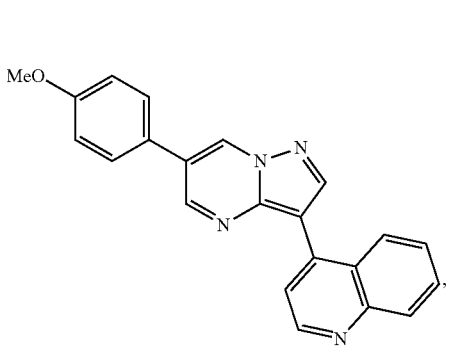
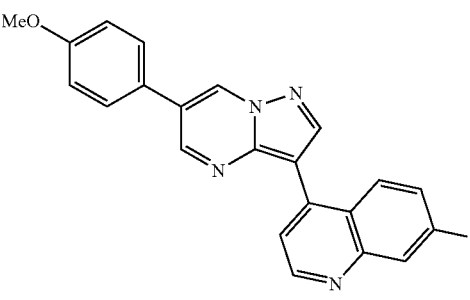

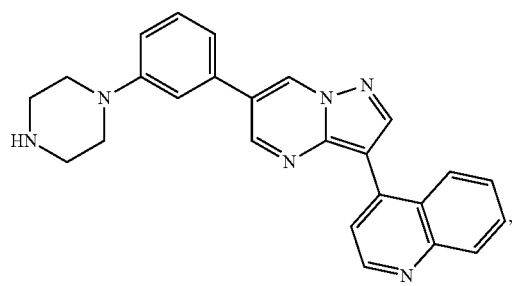
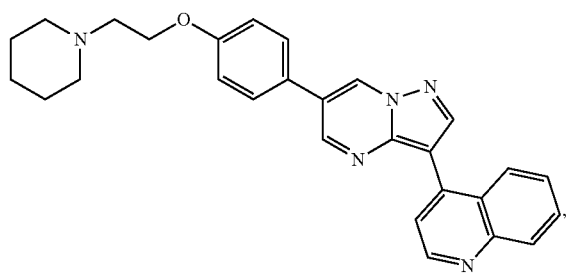
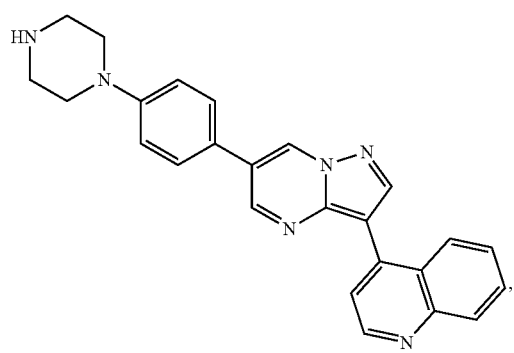
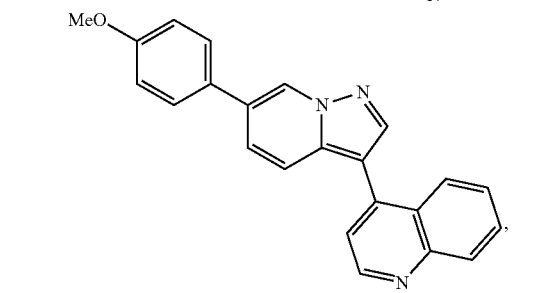
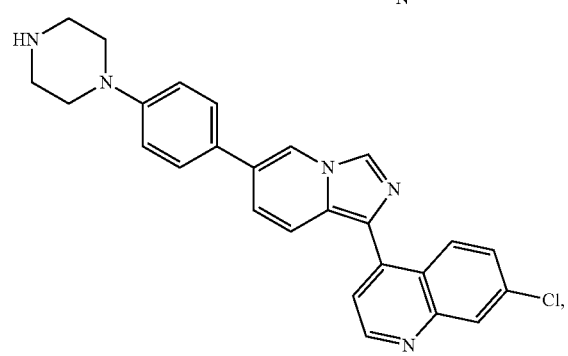
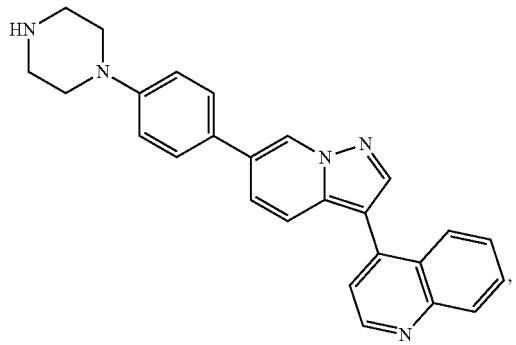
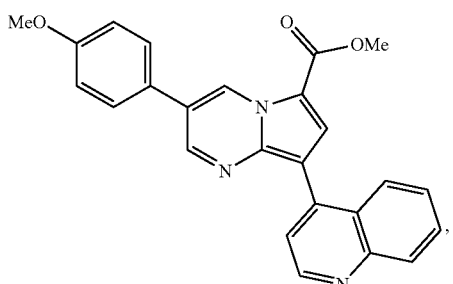
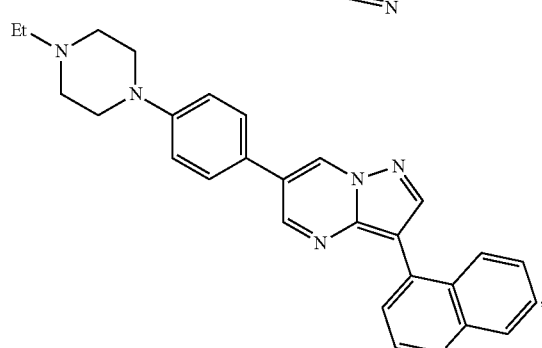
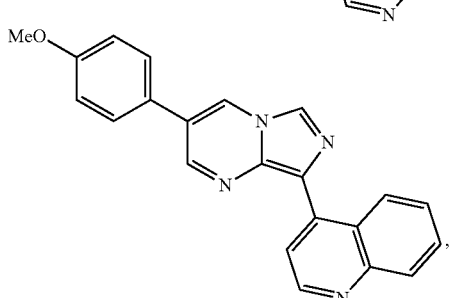
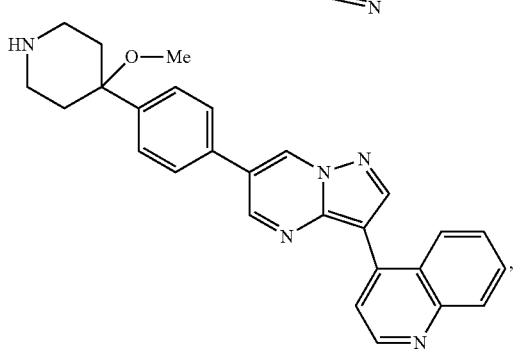

-continued

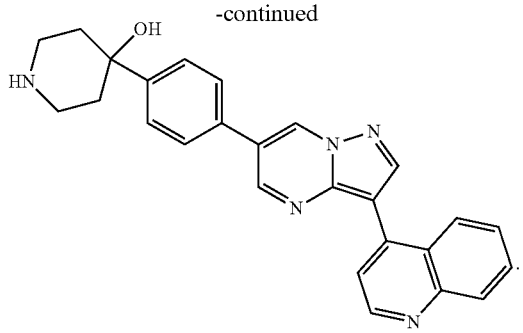

The compounds of Formula I and Formula II are disclosed in US 2011/0053930 A1.

These agents could be applied to prevent cartilage calcification after clinical repair procedures, for example knee cartilage repair. In order to use these agents to prevent calcification in the repair of a focal lesion, a prolonged and local exposure to these agents would be required. Disclosed herein is a system capable of a localized and sustained release.

The system is based on polymer microparticles, such as PLGA microparticles, in which particle preparation parameters are designed to modify the release profile of the BMP I inhibitors. Such microparticles (MPs) may be incorporated in the clotting blood during microfracture, or within a scaffold seeded with chondrocytes or MSCs, for highly localized local and sustained delivery of the BMP I inhibitor to specifically block chondrocyte terminal differentiation.

Dorsomorphin has been encapsulated in PLGA-based MPs of micrometer scale dimensions. As the particles degrade, dorsomorphin is released generating a local concentration within the range required to prevent local calcification. To confirm this, human osteochondral plugs (3 mm by 3 mm by 8 mm of a cartilage and bone biopsy-like sample) have been forced to calcify using triiodothyronine (T3) and then exposed to dorsomorphin. A calcification assay (ALP assay) and real time-PCR confirmed that the dorsomorphin concentration arrested the calcification process.

Applications for the systems disclosed herein for avoiding undesired calcifications are numerous. Ectopic calcification, i.e., the biomineralization of soft tissues that would normally not ossify, affects a variety of tissues, from vasculature, to tendons/ligaments, to muscle tissues and invasive surgeries are often required to remove the calcified tissue. Calcification may also be an issue in regenerative medicine when engineered constructs are implanted to substitute damaged tissue but they start to ossify instead.

Local delivery of BMP I receptor inhibitors could play a key role in improving current reparative therapies. Specifically, in cartilage repair procedures the formation of calcified cartilage or osteophytes may be a significant issue requiring follow up surgery that could be avoided by the systems disclosed herein. The systems could also have additional application in pathologies in which ectopic calcification or heterotopic ossification affects other tissues (skin, kidney, blood vessels, hearth, tendons/ligaments, muscles, etc.), for instance degenerative calcific aortic stenosis that is one of the most common valvular lesion encountered in clinical cardiology. A further use includes inhibition of the formation of intralesional osteophytes.

In certain embodiments the loaded microparticles may be used for treating a subject suffering from or susceptible to heterotopic ossification conditions. The subject may have been diagnosed with, or determined to be suffering from, an heterotopic ossification condition. In certain embodiments, the subject may have active, ongoing, tissue ossification or calcification.

For example, the loaded microparticles disclosed herein may also be used for treating traumatic brain injury (particularly treating or preventing heterotopic ossification in the elbow, shoulder and/or hip after traumatic brain injury), cerebrovascular accident, paraplegia or quadriplegia, heterotopic ossification in the hip after spinal injury, poliomyelitis, Guillain-Barre syndrome, muscle hematoma, joint dislocation, post-hip or knee arthroplasty (particularly contiguous with or near to the hip after hip replacement), surgical scars (particularly abdominal scars after surgery), severe burns (particularly treating or preventing heterotopic ossification in the elbow and/or other joints after severe burns), secondary osteoma cutis, atherosclerosis (particularly treating or preventing heterotopic ossification in coronary arteries in atherosclerosis), valvular heat disease (particularly treating or preventing heterotopic ossification following implantation of a heart valve substitute), traumatic amputations (particularly treating or preventing heterotopic ossification in muscle after a traumatic amputation), ankylosing spondylitis, psoriatic arthritis, osteoarthritis (particularly osteoarthritic damage to cartilage), seronegative arthropathies, diffuse idiopathic skeletal hyperostosis, post-arthroplasty, pressure ulcers, urinary tract infections, arthrofibrosis, or glioma. The loaded particles are particularly useful for locally treating in a confined space or region of need such as surgical scars, severe burns, or cartilage repair.

In certain embodiments, the amount of agent loaded into the microparticles may be from 0.1 ng to 10 mg, more particularly 100 ng to 1000 µg, and most particularly, 1 to 100 µg agent per mg of microparticles.

The microparticle system disclosed herein may provide for sustained release of an agent. The agent release can be linear or non-linear (single or multiple burst release). In certain embodiments, the agent may be released without a burst effect. For example, the sustained release may exhibit a substantially linear rate of release of the therapeutic agent in vivo over a period of at least 120 days, more particularly at least 60 days, and most particularly at least 20 days. By substantially linear rate of release it is meant that the therapeutic agent is released at a rate that does not vary by more than about 20% over the desired period of time, more usually by not more than about 10%. It may be desirable to provide a relatively constant rate of release of the agent from the delivery system over the life of the system. For example, it may be desirable for the agent to be released in amounts from 0.001 to 2 ng per day, more particularly 0.1 to 1 ng per day, for the life of the system. However, the release rate may change to either increase or decrease depending on the formulation of the polymer microparticle. The desired release rate and target drug concentration can vary depending on the particular therapeutic agent chosen for the drug delivery system, and the subject's health.

The polymers for the microparticle may be bioerodible polymers so long as they are biocompatible. Preferred bio-erodible polymers are polyhydroxyacids such as polylactic acid and copolymers thereof. Illustrative polymers include poly glycolide, poly lactic acid (PLA), and poly (lactic-co-glycolic acid) (PLGA). Another class of approved biodegradable polymers is the polyhydroxyalkanoates.

Other suitable polymers include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene polyethylene glycol), poly(ethylene oxide), poly(ethylene terephthalate), poly(vinyl alcohols), poly(vinyl acetate), poly vinyl chloride polystyrene, polyvinylpryrrolidone, alginate, poly(caprolactone), dextran and chitosan.

The percent loading of an agent may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA. The preferred polymer is a PLGA copolymer or a blend of PLGA and PLA. The molecular weight of PLGA is from about 10 kD to about 80 kD, more preferably from about 10 kD to about 35 kD. The molecular weight range of PLA is from about 20 to about 30 kDa. The ratio of lactide to glycolide is from about 75:25 to about 50:50. In one embodiment, the ratio is 50:50.

Illustrative polymers include, but are not limited to, poly(D,L-lactic-co-glycolic acid) (PLGA, 50:50 lactic acid to glycolic acid ratio, $M_n$=10 kDa, referred to as 502H); poly(D,L-lactic-co-glycolic acid) (PLGA, 50:50 lactic acid to glycolic acid ratio, $M_n$=25 kDa, referred to as 503H); poly(D,L-lactic-co-glycolic acid) (PLGA, 50:50 lactic acid to glycolic acid ratio, $M_n$=30 kDa, referred to as 504H); poly(D,L-lactic-co-glycolic acid) (PLGA, 50:50 lactic acid to glycolic acid ratio, $M_n$=35 kDa, referred to as 504); and poly(D,L-lactic-co-glycolic acid) (PLGA, 75:25 lactic acid to glycolic acid ratio, $M_n$=10 kDa, referred to as 752).

In certain embodiments, the polymer microparticles are biodegradable.

The agent-loaded microparticles may have a volume average diameter of 10 nm to 500 μm, more particularly 5 to 20 μm. The agent-loaded microparticles may be pore-less or they may contain varying amounts of pores of varying sizes, typically controlled by adding NaCl during the synthesis process.

The agent-loaded microparticle fabrication method can be single or double emulsion depending on the desired encapsulated agent solubility in water, molecular weight of polymer chains used to make the microparticles (MW can range from ~1000 Da to over 100,000 Da) which controls the degradation rate of the microparticles and subsequent drug release kinetics.

In some embodiments, the methods disclosed herein involve administering to a subject in need of treatment a pharmaceutical composition, for example a composition that includes a pharmaceutically acceptable carrier and a therapeutically effective amount of the loaded microparticles disclosed herein. The compositions or loaded microparticles may be administered, for example, orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The loaded microparticles are preferably formulated into suitable pharmaceutical preparations such as tablets, capsules, or elixirs for oral administration or in sterile solutions or suspensions for parenteral administration.

In some embodiments, one or more of the disclosed loaded microparticles are mixed or combined with a suitable pharmaceutically acceptable carrier to prepare a pharmaceutical composition. Pharmaceutical carriers or vehicles include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., 21$^{st}$ Edition (2005), describes exemplary compositions and formulations suitable for pharmaceutical delivery of the compounds disclosed herein. In addition, the loaded microparticles may be formulated as the sole pharmaceutically active ingredient in the composition or may be combined with other active ingredients.

Upon mixing or addition of the loaded microparticles to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the loaded microparticles in the selected carrier or vehicle. Where the loaded microparticles exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the inhibitors, such as salts or prodrugs may also be used in formulating effective pharmaceutical compositions. The disclosed loaded microparticles may also be prepared with carriers that protect them against rapid elimination from the body, such as time-release formulations or coatings. Such carriers include controlled release formulations, such as, but not limited to, microencapsulated delivery systems.

The disclosed loaded microparticles and/or compositions can be enclosed in multiple or single dose containers. The loaded microparticles and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed loaded microparticle and a second therapeutic agent for co-administration. The loaded microparticles and second therapeutic agent may be provided as separate component parts. A kit may include a plurality of containers, each container holding one or more unit dose of the loaded microparticles. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The loaded microparticles are included in the pharmaceutically acceptable carrier in an amount sufficient to exert a therapeutically useful effect in the absence of undesirable side effects on the subject treated. A therapeutically effective concentration may be determined empirically by testing the loaded microparticles in known in vitro and in vivo model systems for the treated disorder. In some examples, a therapeutically effective amount of the loaded microparticles is an amount that lessens or ameliorates at least one symptom of the disorder for which the loaded microparticle is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 0.1 mg to 1000 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed loaded microparticles or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

The loaded microparticles are especially suitable for local and/or sustained delivery. For local delivery, the loaded microparticles are applied directly to the tissue or organ for which treatment is sought. The effect of local delivery is limited primarily to the tissue or organ to which the loaded microparticles are applied. For example, local delivery may be accomplished through the use of compositions such as liniments, lotions, drops, ointments, creams, suppositories, emulsions, solutions, suspensions and the like. Local delivery can also be accomplished using special delivery devices such as catheters, syringes or implantables designed to convey drug to a specific region in the body.

The delivery composition may be a topical, syringable, or injectable formulation; and is suitable for local delivery of the active agent. For topical administration, the delivery composition is applied directly where its action is desired. Methods for topical delivery include the use of ointments, creams, emulsions, solutions, suspensions and the like. In other embodiments, the delivery composition is administered by application through a cannula, by injection, or as part of a lavage. Compositions for these types of local delivery can include solutions, suspensions and emulsions.

Examples of local administration include, but are not limited to, epicutaneous administration (i.e., application onto the skin); inhalation; as an enema for local administration to the bowel; ocular, for example, as eye drops for local administration to the conjunctiva; aural, for example, as ear drops; or intranasal. In other embodiments, an active agent can be administered locally from a device such as a balloon catheter. In another embodiment, local administration includes the lavage of an open wound, the lavage containing delivery compositions described herein with antimicrobials or other wound healing medicaments.

In yet another embodiment, the loaded particles can be administered as a coating on an article for implantation. Such articles include polymer scaffolds containing stem/progenitor cells, stents, shunts, and the like.

The loaded microparticles may also be delivered via an impregnated or coated device such as a stent, for example, or an artery-inserted cylindrical polymer. The loaded microparticles may be administered, for example, by local delivery from the struts of a stent, from a stent graft, from grafts, or from the cover or sheath of a stent.

In some embodiments, the loaded microparticles are admixed with a matrix and formed into an implantable drug depot. Such a matrix may be a polymeric matrix. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the active compound.

The loaded microparticles can also be included in a hydrogel matrix for administration to a subject, particularly for local and sustained delivery of the inhibitors disclosed herein.

In some embodiments, the pharmaceutical composition is formulated for injection containing the loaded microparticles and a pharmaceutical excipient suitable for injection. The forms in which the compositions may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the loaded microparticles in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Another exemplary formulation for use in the methods disclosed herein employs transdermal delivery devices ("patches"). Such transdermal patches may be used to provide continuous or discontinuous infusion of loaded microparticles in controlled amounts, either with or without another agent.

In certain embodiments, the loaded microparticles may be administered in a scaffold, for instance filling a defect in cartilage (it could be a polymeric scaffold or a hydrogel) or by covering a burn with a smear of gelatin which has the particles inside or of fibrin glue or with a membrane patch. Transdermal microneedles could also be a way of administering the microparticles as well as skin patches.

Examples

Dorsomorphin Microparticle Fabrication
Reagents:
   4.2 kDa 50:50 PLGA
   DI $H_2O$
   Dichloromethane (DCM)
   4% Polyvinyl Alcohol (PVA)
1) Surfactants: make up 2% (60 ml/100 ml beaker: 30 ml of PVA in 30 ml of DI $H_2O$) and 1% PVA solutions (80 ml/in 250 ml beaker: 20 ml of PVA in 60 ml of DI $H_2O$).
2) Prepare 0.5 ml of 0.5 mg/ml dorsomorphin in DMSO.
3) Prepare 5% PLGA solution (200 mg PLGA; 4 ml DCM).
4) Combine dorsomorphin and PLGA solutions.
5) Place the 100 ml beaker of 2% PVA under the homogenizer & the 250 ml beaker of 1% PVA on magnetic stirrer, spinning at 500 rpm.
6) Pour dorsomorphin/PLGA solution into the 2% PVA solution that is being homogenized at 2700 rpm.
7) Homogenize for 1 min at 2700 rpm.
8) Immediately pour into 1% PVA solution that is being stirred at 500 rpm.
9) Stir for 3 hours to let DCM evaporate, after which remove and wash in D.I. water 4 times.
10) Spin/wash with DI $H_2O$ in 50 ml falcon tubes to remove PVA. Spin at 1000 rpm for 5 minutes then decant.
11) Repeat spin/wash at least 3 times.
12) Collect/resuspend microparticles in less than 5 ml DI $H_2O$ and place in scintillation vial (weight vial beforehand)
13) Freeze in −80 C freezer
14) Transfer in the lyophilizer and keep it there for 2-3 days.

T3 Induces Hypertrophy Primary Chondrocytes Hypertrophy

In autologous chondrocytes implantation (ACI) chondrocytes are implanted in a local cartilage defect. In an in vitro model of ACI based on a small osteochondral unit, as the one we use, a central cartilage defect would be filled with chondrocytes in a hydrogel. To simulate conditions of calcification, the chondrocytes will be pre-cultured in a hypertrophy inducing medium. After seeding, both native cartilage and implanted chondrocytes would be exposed to chondrogenic medium. We have previously shown that T3 induces hypertrophy in MSCs that underwent chondrogenic differentiation. Here we show that T3 is effective to induce primary chondrocytes hypertrophy that is maintained even after exposure to chondrogenic medium (see FIGS. 7A-7F). Chondrogenic medium and osteogenic medium are used as comparison.

A Calcification Model

A calcification model was developed inducing hypertrophy of human chondrocytes (monolayer culture and 3D photocrosslinkable gelatin constructs) or osteochondral (OC) tissue plugs by exposure to the hormone tri-iodothyronine (T3). Human osteoblasts were used as a positive control. Both chondrocytes, and osteoblasts (cells and constructs) were treated with 3 different conditions for each experiment: Chondrogenic Medium (CM), Osteogenic Medium (OM), and Hypertrophic Medium (HM).

For the 3D gelatin constructs, chondrocytes were harvested from the knee of a 65-year old male donor and osteoblasts from the hip of a 65-year old male donor. After 14 days and 21 days, 1 group of constructs in both the positive control and the experimental group were switched to chondrogenic media until the end of the 28-day experiment. Another group of constructs for each condition was carried out for the total 28 days. Histology and RT-PCR (COL1, COL2, ACAN, ALP, RUNX-2, COL10, OCN, MMP13) were performed to confirm the presence or absence of hypertrophy. The results are shown in FIGS. 8A-8I.

In Vivo Heterotopic Ossification after MPC and BMP2 Injection

Heterotopic ossification (HO), the formation of mature bone in the soft tissues, is a frequent complication following trauma. The pathogenesis of HO is not well understood, but is hypothesized to involve an inappropriate cellular response to the inflammatory environment and specific osteogenic signals therein. We have previously isolated and characterized a population of mesenchymal progenitor cells (MPCs) derived from human blast-traumatized muscle (BDM-MSC) that may represent the cellular component of the disease.

Figure 9:
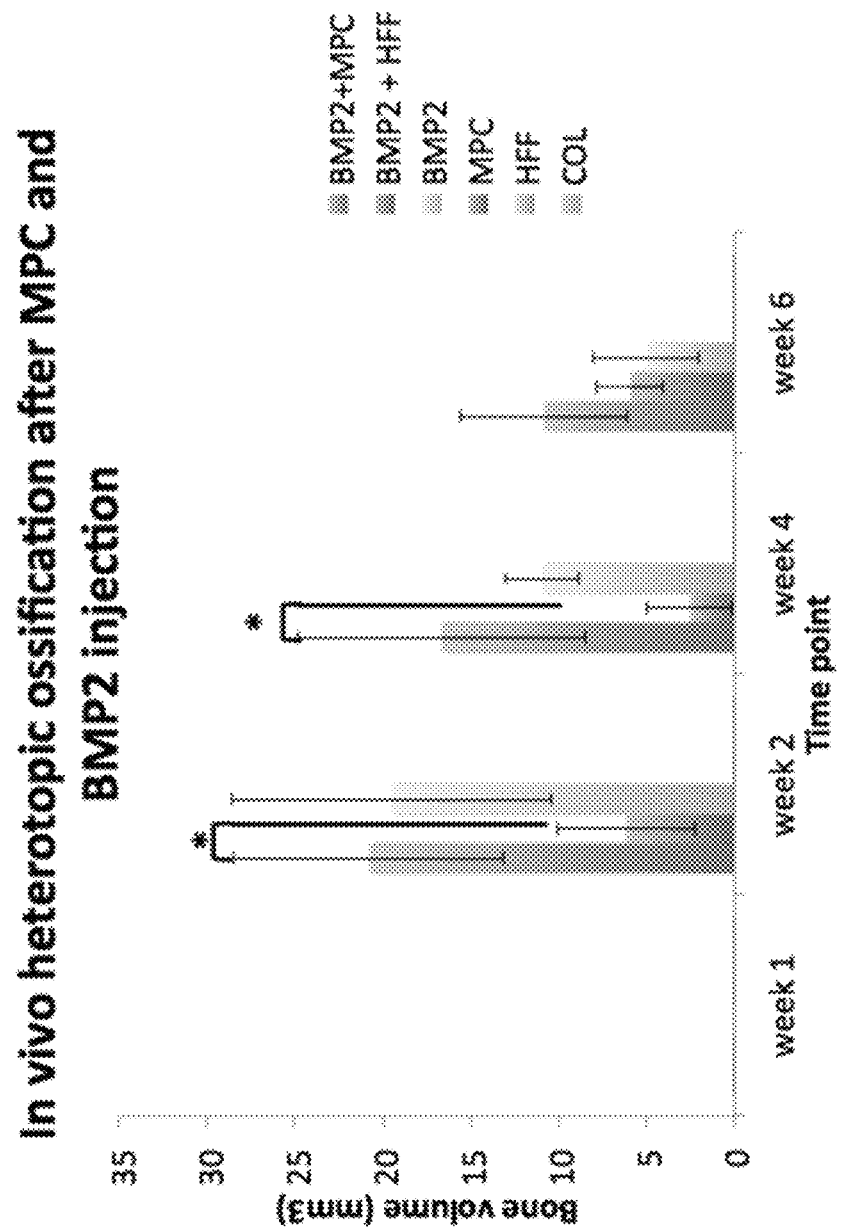
FIG. 9 is a graph of bone volume determined by µCT in an in vivo mouse model. Formation of ectopic bone nodules in the hind limbs of SCID mice injected with muscle-derived multipotent progenitor cells (MPC) with or without BMP2 as compared to those injected with human foreskin fibroblasts (HFF) with or without BMP2, at 1, 2, 4 and 6 weeks.

Formation of ectopic bone nodules in the hind limbs of SCID mice injected with MPC+/−BMP2 as compared to those injected with human foreskin fibroblasts (HFF)+/− BMP2 is shown in FIG. 9. Bone volume is determined by μCT. Injection of collagen served as a negative control.

These results indicate that BMP induces significantly more osteogenesis by MPCs than HFF. BMP alone induces osteogenesis at levels comparable to that measured in MPC+ BMP injected samples at week 2 and 4 after injection. However, HO lesions induced by BMP alone were significantly reduced after 6 weeks as compared to samples with MPCs present, indicating that the MPCs are playing a substantial role in the production and maintenance of the HO lesions.

Inhibition of muscle-derived multipotent progenitor cells (MPC) osteogenesis in 2D by dorsomorphin (DM) (2.5 mM) as shown by alizarin red staining (Mag=10×) is shown in FIG. 10. MPCs from the same donor were plated and cultured in different conditions. Controls received only regular growth medium, the BMP+ group were exposed to medium additioned with BMP which is a strong inducer of osteogenesis, the DM+ groups were exposed to medium additioned with soluble dorsomorphin to control for effects of dorsomorphin alone, and the test group BMP+DM+ was exposed to medium containing both soluble BMP and soluble dorsomorphin. Media were renewed twice a week. Cells were assessed for osteogenesis/calcification at 1, 3, 5, and 7 weeks. Osteogenesis/deposition of calcium was assessed by alizarin red staining, a common histological staining procedure. The control group exhibited a moderate tendency to calcification even without BMP stimulation, as indicated by the progressive reddening over time. Exposure to BMP induced a strong osteogenic/calcification phenotype, marked by the strong red staining especially at 7 weeks. Dorsomorphin alone seemed to inhibit even the natural tendency of bone marrow-derived MSCs to calcify. When both BMP and dorsomorphin were added to the media, no calcification happened, indicating that dorsomorphin is able to inhibit calcification even when it is potently induced by BMP as would occur in vivo.

Inhibition of BMD-MSC osteogenesis in 2D culture by dorsomorphin (DM) is shown in FIG. 11. Phase contrast images of alizarin red stained cultures treated with BMP (B), DM, and BMP+DM (D) as compared to control (A) and DM (C) cultures. The test was performed as the one in FIG. 10 but using bone marrow-derived MSCs and with a sole time point of 21 days. In this case as well, BMP exposure induced a strong calcium deposition, which was completely inhibited by the addition of soluble dorsomorphin in solution.

Formation of ectopic bone nodules in the hind limbs of SCID mice injected with MPC+BMP2+/−DM. DM was delivered in solution or in micro particles. The DM was loaded into PLGA microparticles. Bone volume is determined by µCT.

Micro-CT 3D reconstructions HO lesions in vivo following injection of (A) MPC/BMP2+DM in microparticles (mp), (B) MPC/BMP2+ soluble (s) DM, and (C) MPC/BMP2 alone. All scans were normalized to the device hydroxy apatite standard (in vivo µCT 40; ScanCo).

Figure 4:
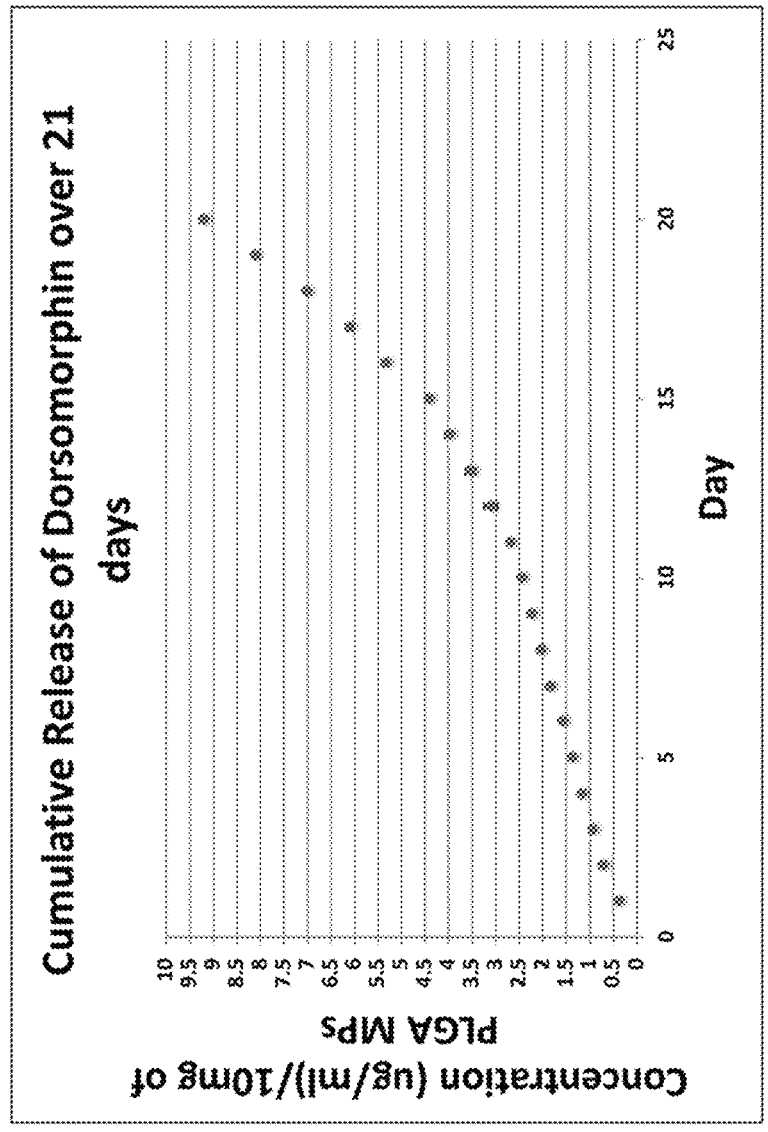
FIG. 4 is a graph depicting dorsomorphin release. 10 mg of PLGA microparticles containing dorsomorphin have been suspended in 1 ml of PBS. Each day, PBS is removed and stored at −20° C. until examination and the microparticles are resuspended in 1 ml of PBS. Each experiment is repeated at least in triplicate. Periodically, the collected PBS is examined by HPLC to quantify against a standard concentration curve the amount of dorsomorphin released. The graph reports the values of the cumulative release of dorsomorphin over a 20 day period in micrograms per milliliter for each 10 mg of microparticles.
Figure 5:
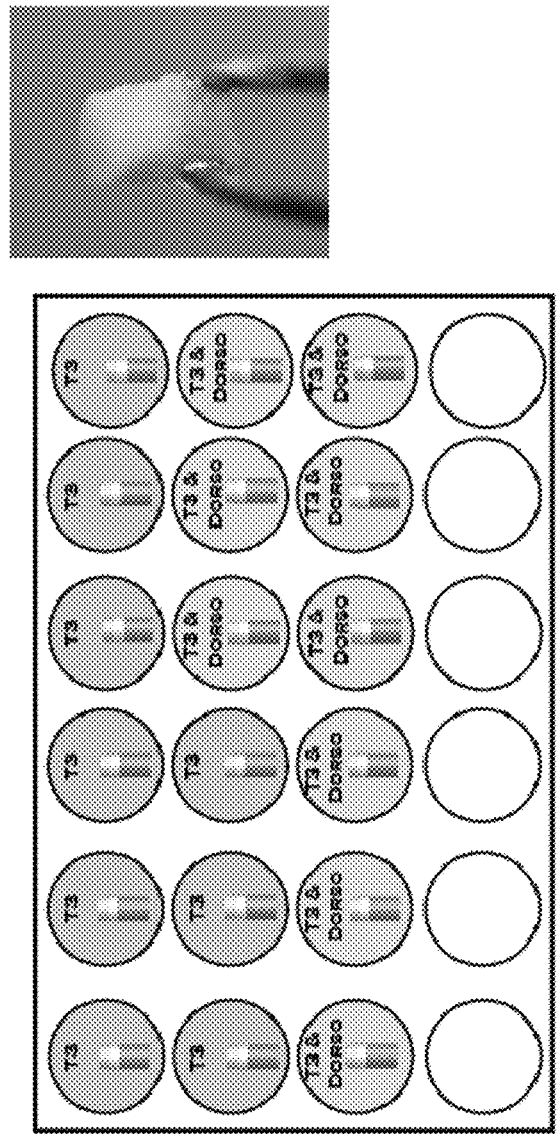
FIG. 5 represents the outline for testing of preventing calcification. Experimental design to test the effects of triiodothyronine in inducing calcification and of dorsomorphin in inhibiting calcification in human osteochondral biopsies, an example of which is depicted on the right.
Figure 6:
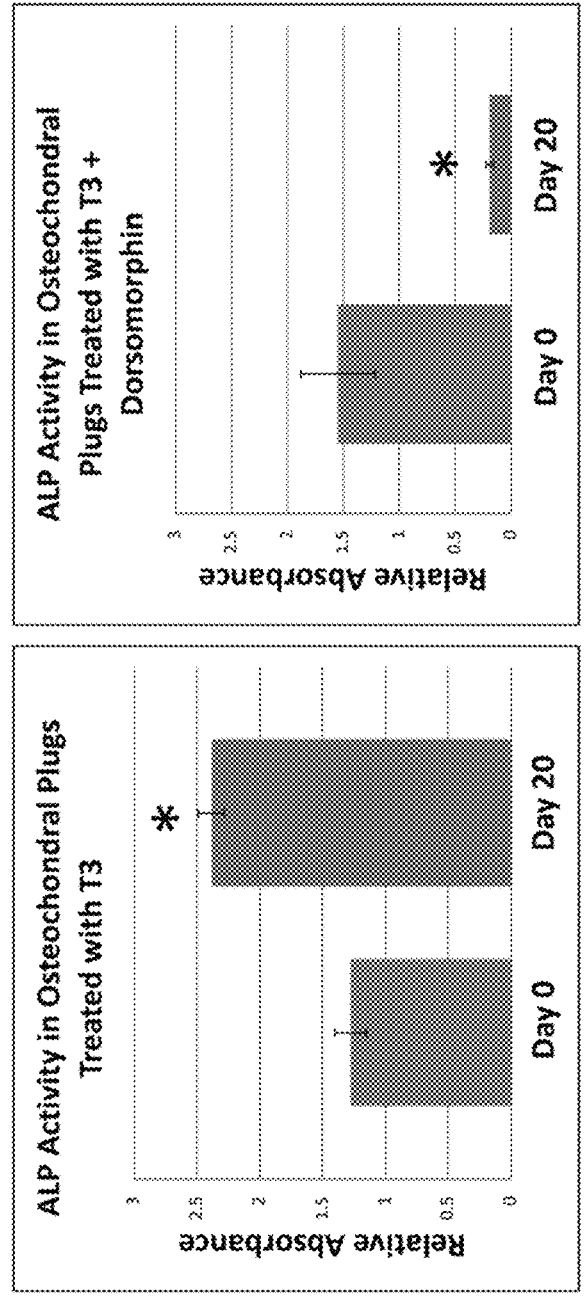
FIG. 6 is two graphs depicting ALP activity. The graphs represent the level of ALP activity in the osteochondral constructs media measured with a colorimetric ALP assay for the samples outlined in the previous figure. The first graph reports a statistically significant ($p<0.05$) increase in ALP activity after treatment with triiodothyronine (T3) between day 0 and day 20. The second graph reports a statistically significant ($p<0.05$) decrease in ALP activity between day 0 and day 20 when samples are treated with both triiodothyronine and dorsomorphin.
Figure 12:
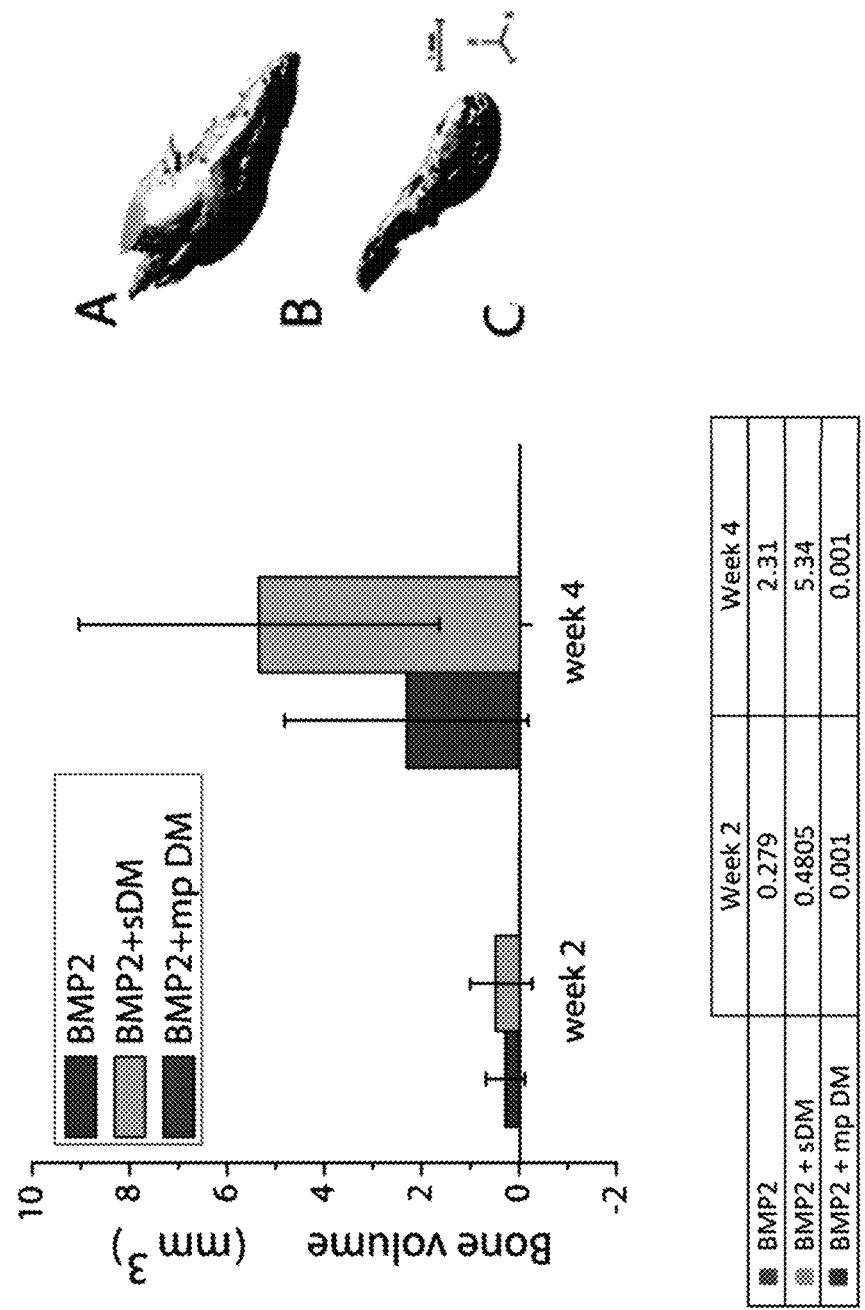
FIG. 12 is bone volume, determined by µCT, formed ectopically in the hind limbs of SCID mice injected with MPC+BMP2+/−dorsomorphin (DM). DM was delivered in colution (sDM) or in micro particles (mpDM). Representative µCT 3D reconstructions of heterotopic ossification (HO) inhibition of BMP2-stimulated MPC osteogenesis in vivo by dorsomorphin. HO lesions in vivo following injection of MPC/BMP2 and (A) soluble (s) DM, (B) alone, and (C) DM in microparticles (no calcification registered). All scans were normalized to the device hydroxyapatite standard (in vivo µCT 40; ScanCo).

These results shown in FIG. 12 indicate that the injection of 25 ng/ml BMP induces MPC osteogenesis within the muscle tissue. The co-injection of microparticles loaded with DM inhibited this BMP2-induced MPC heterotopic ossification. sDM stands for soluble dorsomorphin, that is dorsomorphin that is solely injected with the cells in the mouse limb. sDM rapidly diffuses away or is all metabolized by cells in a short time, and it then has no long term effect on the locally injected cells. Mp DM stands for microparticles containing dorsomorphin. As the particles degrade, dorsomorphin is released locally and the injected cells are continually exposed to dorsomorphin coming in low overall doses but sufficient local concentrations to induce a long term effects on injected cells that do not calcify (hardly any heterotopic bone volume is visible). A microparticles release system is then necessary for dorsomorphin to be effective. The microparticles were loaded as described in the previous protocol and are particles from the same batch from which particles were taken to perform the release profile in FIG. 4.

In view of the many possible embodiments to which the principles of the disclosed embodiments may be applied, it should be recognized that the illustrated embodiments are only examples and should not be taken as limiting the scope of the invention.

What is claimed is:

1. A therapeutic scaffold comprising (i) BMP I inhibitor-loaded microparticles and (ii) chondrocytes.

2. The scaffold of claim 1, wherein the inhibitor is dorsomorphin.

3. The scaffold of claim 1, wherein the inhibitor is LDN-193189, SB505124, noggin, cordin, or gremlin.

4. The scaffold of claim 1, wherein the inhibitor is a compound, or a pharmaceutically acceptable salt thereof, represented by formula I:

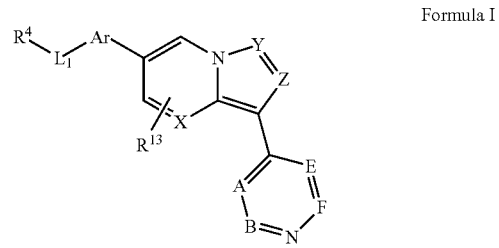

Formula I wherein X is selected from $CR^{15}$ and N; Y is selected from $CR^{15}$ and N; Z is selected from $CR^3$ and N; Ar is selected from substituted or unsubstituted aryl and heteroaryl; $L_1$ is absent or selected from substituted or unsubstituted alkyl and heteroalkyl; A and B, independently for each occurrence, are selected from $CR^{16}$ and N; E and F, independently for each occurrence, are selected from $CR^5$ and N; $R^3$ represents a substituent; $R^4$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido; $R^5$, independently for each occurrence, represents a substituent selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, or two occurrences of $R^5$ taken together with the atoms to which they are attached form a substituted or unsubstituted 5- or 6-membered cycloalkyl, heterocycloalkyl, aryl, or heteroaryl ring; $R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido; $R^{15}$, independently for each occurrence, represents a substituent, selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido; and $R^{16}$, independently for each occurrence, represents a substituent selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

5. The scaffold of claim 1, wherein the inhibitor is a compound, or a pharmaceutically acceptable salt thereof, represented by formula II:

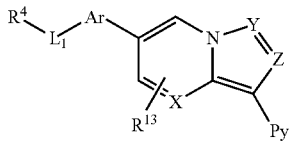

wherein X is selected from $CR^{15}$ and N; Y is selected from $CR^{15}$ and N; Z is selected from $CR^3$ and N; Ar is selected from substituted or unsubstituted aryl and heteroaryl; $L_1$ is absent or selected from substituted or unsubstituted alkyl and heteroalkyl; Py is substituted or unsubstituted 4-pyridinyl or 4-quinolinyl; $R^3$ represents a substituent selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido; $R^4$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido; $R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido; and $R^{15}$, independently for each occurrence, represents a substituent selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamide.

6. The scaffold of claim 1, wherein the microparticles comprise poly glycolide, poly lactic acid (PLA), poly (lactic-co-glycolic acid) (PLGA), or a combination thereof.

7. The scaffold of claim 6, wherein the loaded microparticles have a volume average diameter of 5 to 20 μm.

8. The scaffold of claim 7, wherein the inhibitor is dorsomorphin.

9. The scaffold of claim 1, wherein the loaded microparticles have a volume average diameter of 10 nm to 500 μm.

10. The scaffold of claim 1, wherein the loaded microparticles have a volume average diameter of 5 to 20 μm.

11. The scaffold of claim 1, further comprising mesenchymal stem cells.

12. The scaffold of claim 1, wherein the scaffold is a stent or shunt.

13. The scaffold of claim 1, wherein the BMP I inhibitor-loaded microparticles and the chondrocytes are located on a surface of the scaffold.

* * * * *